(12) United States Patent
McGlennen et al.

(10) Patent No.: US 8,594,948 B2
(45) Date of Patent: Nov. 26, 2013

(54) APPARATUS AND METHODS FOR MEDICAL TESTING

(76) Inventors: Ronald C. McGlennen, Edina, MN (US); Naomi M. Williamson, Fridley, MN (US); Aaron M. Franks, Eden Prairie, MN (US); David J. Olson, Minnetrista, MN (US); Robert P. Schuldt, Eagan, MN (US); Vickie Matthias-Hagen, Hugo, MN (US)

( * ) Notice: Subject to any disclaimer, the term of this patent is extended or adjusted under 35 U.S.C. 154(b) by 0 days.

(21) Appl. No.: 12/833,209

(22) Filed: Jul. 9, 2010

(65) Prior Publication Data

US 2011/0178814 A1    Jul. 21, 2011

Related U.S. Application Data

(63) Continuation-in-part of application No. 11/389,435, filed on Mar. 23, 2006, now abandoned, and a continuation-in-part of application No. 10/409,337, filed on Apr. 7, 2003, now abandoned.

(60) Provisional application No. 60/664,764, filed on Mar. 23, 2005.

(51) Int. Cl.
*G06F 7/00* (2006.01)

(52) U.S. Cl.
USPC ............... 702/19; 702/20; 703/11; 707/700; 435/6.1; 435/7.1; 436/501

(58) Field of Classification Search
None
See application file for complete search history.

(56) References Cited

U.S. PATENT DOCUMENTS

| | | | |
|---|---|---|---|
| 5,334,499 A | | 8/1994 | Burdict et al. |
| 5,631,844 A | | 5/1997 | Margrey et al. |
| 5,701,904 A | | 12/1997 | Simmons et al. |
| 5,795,722 A | | 8/1998 | Lacroix et al. |
| 5,814,448 A | | 9/1998 | Silverstein et al. |
| 5,818,448 A | | 10/1998 | Katiyar |
| 5,955,351 A | | 9/1999 | Gerdes et al. |
| 5,973,137 A | | 10/1999 | Heath |
| 5,985,559 A | | 11/1999 | Brown |
| 5,987,519 A | | 11/1999 | Peifer et al. |
| 6,054,277 A | | 4/2000 | Furcht et al. |
| 6,063,566 A | | 5/2000 | Joyce |
| 6,088,690 A | | 7/2000 | Gounares et al. |
| 6,132,724 A | | 10/2000 | Blum |
| 6,145,991 A | * | 11/2000 | McClure et al. ............... 351/246 |
| 6,153,425 A | | 11/2000 | Kozwich et al. |
| 6,194,149 B1 | | 2/2001 | Neri et al. |
| 6,210,880 B1 | | 4/2001 | Lyamichev et al. |
| 6,214,545 B1 | | 4/2001 | Dong et al. |
| 6,234,964 B1 | | 5/2001 | Iliff |
| 6,256,613 B1 | | 7/2001 | Falchuk et al. |
| 6,258,543 B1 | | 7/2001 | Gerdes et al. |
| 2004/0014097 A1 | | 1/2004 | McGlennen et al. |
| 2004/0122708 A1 | | 6/2004 | Avinash et al. |
| 2004/0215490 A1 | * | 10/2004 | Duchon et al. ............... 705/2 |
| 2004/0267562 A1 | | 12/2004 | Fuhrer et al. |
| 2005/0262031 A1 | | 11/2005 | Saidi et al. |
| 2006/0278242 A1 | | 12/2006 | McGlennen et al. |
| 2007/0061085 A1 | * | 3/2007 | Fernandez ............... 702/20 |

FOREIGN PATENT DOCUMENTS

| WO | WO 99/04043 | 1/1999 |
|---|---|---|
| WO | WO 01/28415 | 4/2001 |
| WO | WO 03/027236 | 4/2003 |

OTHER PUBLICATIONS

McGlennen, MD, Ronald C., Integrate Molecular Diagnostics: Created a Strategic Menu, MLO, [online] [retrieved on Dec. 2007] [retrieved from] <www.mlo-online.com>, pp. 26-28, 52.
McGlennen, MD, Ronald C., Miniaturization Technologies for Molecular Diagnostics, Clinical Chemistry, vol. 47, No. 3, 2001, pp. 393-402.
Supplementary Search Report for related European patent application 02 76 3658, 2007.
International Search Report for related International Application No. PCT/US2002/029628, 2006.
International Preliminary Exam Report for related International Application No. PCT/US2002/029628, 2007.

* cited by examiner

*Primary Examiner* — Mary Zeman
(74) *Attorney, Agent, or Firm* — Billion & Armitage; Patti J. Jurkovich

(57) ABSTRACT

Apparatus and methods for practicing telemedicine in the form of software systems acting over a network and kits containing laboratory supplies and equipment to organize the laboratory operations and interpret the results of molecular diagnostic testing are disclosed. At least two computers in communication over the Internet or other network are used, a remote computer located at a remote site and a central server located at a central site. The remote site may be geographically distant from the central site. A specimen is procured from a patient proximate to the remote site. Laboratory operations are conducted on the specimen at the remote site. The laboratory data resulting from the laboratory operations is interpreted by an expert reviewer who may be located at the central site, and a report is then transmitted back to the remote site.

21 Claims, 25 Drawing Sheets

FIG. 3

| FIG. 3A |
|---|
| FIG. 3B |

| | | CYSTIC FIBROSIS | |
|---|---|---|---|
| | | PATIENT WELLS | 3 |
| | | TOTAL WELLS | 5 |
| | | ENZYME DILUTION MIX | |
| | | HPLC H20 | 39.3 UL |
| | | LOADING DYE | 57.8 UL |
| | | DILUTION BUFFER | 11.6 UL |
| | | AMPLI TAQ GOLD | 6.9 UL |
| | | TOTAL | 115.5 UL |
| | | REACTION MIXES A,D | |
| | | PRIMER MIX | 82.5 UL |
| | | ENZYME DILUTION MIX | 27.5 UL |
| | | TOTAL | 110.0 UL |

CYSTIC FIBROSIS WORKSHEET
BATCH ID: 09072004_5_CF
DATE: 02/16/2005 09:53

| EXTRACTION | | SETUP | |
|---|---|---|---|
| DATE: | | DATE: | |
| TECH: | | TECH: | |
| LOT#: | | LOT#: | |

PRINT    CLOSE

| SAMPLE | ACCN# | PATIENT | EXTRACTION ID | PLATE POSITION (S) | GEL POSITION (S) |
|---|---|---|---|---|---|
| | LADDER | | — | | GEL:1 LANE:1 |
| | POS CTL | | — | A1,A2,A3,A4 | GEL:1 LANES:2,3,4,5 |
| | BLK CTL | | — | B1,B2,B3,B4 | GEL:1 LANES:6,7,8,9 |
| | LADDER | | — | | GEL:1 LANE:10 |
| 1 | 1001 | PATIENT, 1 | — | C1,C2,C3,C4 | GEL:1 LANES:11,12,13,14 |
| 2 | 2002 | PATIENT, 2 | — | D1,D2,D3,D4 | GEL:1 LANES:15,16,17,18 |
| | LADDER | | — | | GEL:1 LANE:19 |
| 3 | 3003 | PATIENT, 3 | — | E1,E2,E3,E4 | GEL:1 LANES:20,21,22,23 |

TEST SETUP DATA FIELDS
REAGENT CALCULATOR FIELDS

| | | | | | Extraction Layout | | | | | | | |
|---|---|---|---|---|---|---|---|---|---|---|---|---|
| | | | | | Batch Id:09072004_5_CF | | | | | | | |
| | 1 | 2 | 3 | 4 | 5 | 6 | 7 | 8 | 9 | 10 | 11 | 12 |
| A | 1001 | 9 | 17 | | | | | | | | | |
| B | 2002 | 10 | 18 | | | | | | | | | |
| C | 3 | 11 | | | | | | | | | | |
| D | 4 | 12 | | | | | | | | | | |
| | | | | | | | | | | | | |
| E | 5 | 13 | | | | | | | | | | |
| F | 6 | 14 | | | | | | | | | | |
| G | 7 | 15 | | | | | | | | | | |
| H | 8 | 16 | | | | | | | | | | |

| ACCESS GENETICS CE POSITIVE CONTROL SET: VERSION 3.19 | | | | |
|---|---|---|---|---|
| CF CONTROL SET | LANES WITH BANDS PRESENT | EXPECTED BANDS (TOP TO BOTTOM, LEFT TO RIGHT) | | |
| | | BAND 1 | BAND 2 | BAND 3 |
| A | A | ΔF508 (M) | – | – |
| B | B-B-D | 621+1G>T | ΔF508 (N) | 3120+1G>A |
| C | A-B-C | ΔF508 (M) | ΔF508 (N) | R553X |
| D | B-B | G551D | ΔF508 (N) | – |
| E | A-B-C | ΔF508 (M) | ΔF508 (N) | 3659delC |
| F | B-C | ΔF508 (N) | ΔI507 | – |
| G | B-B-D | 621+1G>T | ΔF508 (N) | 711_1G>T |
| H | A-B-B | ΔF508 (M) | 621+1G>T | ΔF508 (N) |
| J | B-B-D | 621+1G>T | ΔF508 (N) | G85E |
| K | A-B-C | ΔF508 (M) | ΔF508 (N) | A445E |
| L | A-B-D | ΔF508 (M) | ΔF508 (N) | R560T |
| M | A-B | N1303K | ΔF508 (N) | – |
| N | A-B | G542X | ΔF508 (N) | – |
| O | A-B | W1282X | ΔF508 (N) | – |
| P | B-D | ΔF508 (N) | 2789+5G>A | – |
| Q | A-B | 3849+10kbC | ΔF508 (N) | – |
| R | A-B | 1717-1G>A | ΔF508 (N) | – |
| S | B-B | R1162X | ΔF508 (N) | – |
| T | B-B-C | G551D | ΔF508 (N) | R347P |
| U | B-B | ΔF508 (N) | R443W | – |
| W | A-B-B | ΔF508 (M) | R117H | ΔF508 (N) |
| X | A-B-D | ΔF508 (M) | ΔF508 (N) | 2184delA |
| Y | A-B-D | ΔF508 (M) | ΔF508 (N) | 1898+1G>A |
| Z | B-B | 394delTT | ΔF508 (N) | – |
| AA | A-B-D | D1152H | ΔF508 (N) | G85E |
| AB | A-B-C | ΔF508 (M) | ΔF508 (N) | 2183AA>G |
| AC | B-C | ΔF508 (N) | 1078delTT | – |
| AD | A-B-C | ΔF508 (M) | ΔF508 (N) | E60X |

A

| A | B |
|---|---|
| | Apo B 526bp |
| Apo B 423bp | 394delTT 442bp |
| D1152H 367bp | 621+1G>T 383bp |
| 1717-1G>A 329bp | S1251N 323bp |
| | G551D 290bp |
| G542X 279bp | |
| | R117H 243bp |
| W1282X 240bp | |
| N1303K 200bp | R1162X 200bp |
| ΔF508(M) 160bp | ΔF508(N) 160bp |
| 3849+10kbC>T 132bp | R334W 140bp |
| ODC 97bp | ODC 97bp |

ODC = LOWER CONTROL

| FIG. 12 | |
|---|---|
| FIG. 12A | FIG. 12B |

FIG. 12A

Individual: Patient, 2 21 yrs Female
Patient Id: 8652193
Date of Birth: 02/15/1984
Specimen: Pap-ThinPrep
Reason for Test:
History:
Ethnic Background: Asian, Native American Indian Physician/Location: Dr 2 Smith / 2B
Accession: 2748974
Collected: 02/09/2005
Received: 02/09/2005
Reported: 02/09/2005 09:45
Related Info:

Carrier Screening

| Ethnicity | Risk Before CF Test | | Risk After CF Test | Assay Detection rate |
|---|---|---|---|---|
| Northern European Caucasian | 1 in 25 (4.00%) | to | 1 in 241 (0.41%) | 90.0% |
| Southern European Caucasian | 1 in 25 (4.00%) | to | 1 in 81 (1.23%) | 70.0% |

Carrier Screening

| Risk Before CF Test | Risk After CF Test |
|---|---|
| 1 in 1 (100.00%) | 1 in 1 (100.00%) |

*Fig. 13*

|  | | Genotype | |
|---|---|---|---|
| Result: | Prothrombin | Normal(G) | Normal(G) |
|  | Factor V Leiden | Normal(G) | Mutant(A) |
|  | MTHFR | Normal(C) | Normal(C) |

Thrombophilia Risk Assessment

| Genetic Risk | Risk Modifiers |
|---|---|
| Increased approximately 7 times * | Risks are influenced by other medical and environmental factors such as age, smoking, obesity, or immobilization. |

* Risks are compared to that of the general population. These risks are not intended to be multiplied, but are independent variables and are further influenced by other medical and environmental factors.

*Fig. 14*

- Customize Patient Information
Individual: Patient_3  22 yrs  Female
Patient Id: 300-0003
Date of Birth: 09/13/1962
Specimen: Pap-SurePath
Reason for Test:
History:
Ethnic Background:

Physician/Location: Dr 3 Smith / 3B
Accession: 3003
Collected: 09/07/2004
Received: 09/07/2004
Reported:
Related Info:

Customize Patient

[Update Patient Information]  [Close Window]

Patient Information

Patient: Patient_3

Patient Ethnicities
- ☐ Unknown
- ☐ European Caucasian
- ☐ Northern European Caucasian
- ☐ Southern European Caucasian
- ☐ Jewish
- ☐ Jewish (Ashkenazi)
- ☐ Hispanic
- ☐ African American
- ☐ Asian
- ☐ Native American Indian
- ☐ Other

Patient History
- ☐ Pap: Normal
- ☐ Pap: ASCUS
- ☐ Pap: LSIL
- ☐ Pap: HSIL
- ☐ Pap: In situ Carcinoma
- ☐ Pap: Abnormal(Other)

Reason for Test
- ⦿ None
- ○ Abnormal Pap
- ○ Prior History of HPV
- ○ Follow-up for dysplasia

*Fig. 15*

APPARATUS AND METHODS FOR MEDICAL TESTING

CROSS-REFERENCE TO RELATED APPLICATIONS

This application is a Continuation-in-Part of U.S. patent application Ser. No. 11/389,435 filed Mar. 23, 2006, which claims priority from the filing date of U.S. Provisional Patent Application Ser. No. 60/664,764 filed Mar. 23, 2005, the disclosures of which are hereby incorporated by reference herein in their entirety; and is a Continuation-In-Part of U.S. application Ser. No. 10/409,337 filed Apr. 7, 2003; and claims benefit of PCT Application PCT/US/02/29628, filed Sep. 18, 2002.

BACKGROUND OF THE INVENTION

1. Field of the Invention

The present invention relates to business methods and, more particularly, apparatus and methods to bring molecular diagnostic testing to remote sites.

2. Description of the Related Art

Samples of blood, tissue and biologic fluids are analyzed in the clinical laboratory for molecular, chemical and morphologic features that define both health and disease. Molecular diagnostic tests are now conducted in the clinical laboratory. These molecular diagnostic tests are based in sophisticated technologies that analyze the sequence of nucleic acid, DNA and RNA, as well as protein composition and structure. However, only a limited number of clinical laboratories have the facilities and the expertise to conduct and to interpret molecular diagnostic tests. Clinical laboratories having the capability of conducting molecular diagnostic tests are typically found in academic medical centers and in reference lab companies. Patients requiring a molecular diagnostic test would need to travel, perhaps a great distance, to a clinical laboratory having such capability so that the availability of molecular diagnostic tests is restricted. As a result, molecular diagnostic tests are used typically in the care of patients in tertiary care medical settings.

SUMMARY OF THE INVENTION

Apparatus and methods in accordance with the present invention may resolve one or more of the needs and shortcomings discussed above and will provide additional improvements and advantages as will be recognized by those skilled in the art upon review of the present disclosure.

The present invention provides apparatus and methods for practicing telemedicine in the form of software systems acting over the Internet in combination with kits containing laboratory supplies and equipment designed to organize the laboratory operations.

At least two computers in communication over the Internet or other network are used, a remote computer located at a remote site and a central server located at a central site. The remote site may be geographically distant from the central site. A specimen is procured from a patient proximate to the remote site. Patient information, which consists, inter alia, of medical history, pathologic information, family history, lifestyle information, and racial and ethnic background is also obtained from the patient proximate the remote site. A kit is provided to a clinical laboratory at the remote site. The kit contains materials and apparatus necessary for the performance of molecular diagnostic tests. The kit also organizes the conduct of molecular diagnostic tests so that laboratory technicians of varying skill and training are able to accurately conduct the laboratory operations of molecular diagnostic tests at the remote site. The system collects laboratory data resulting from the laboratory operations of a molecular diagnostic test and the patient information into an interpretive data set. This interpretive data set is then transmitted over the Internet or other network from the remote site to the central site. An expert reviewer at the central site then uses an interpretive interface to interpret the interpretive data set. The interpretations of the expert reviewer are collected in a test report. The interpretive interface may generate additional reports. The test report is transmitted back to the remote site to be available to a medical professional located proximate the remote site.

BRIEF DESCRIPTION OF THE DRAWINGS

FIG. 3 illustrates an electronic form displaying patient information data entry fields, including drop down selection options;

FIG. 6B illustrates a representative batch list and shows the assignment of specimens to specific locations in a batch of specimens;

FIG. 6C illustrates the reagent calculator and also shows the assignment of specimens to specific locations in a batch of specimens;

FIG. 6D illustrates the assignment of specimens to specific locations in a batch of specimens during extraction;

FIG. 10 illustrates linked reviewer files and triage status;

Figures 11, 11A:
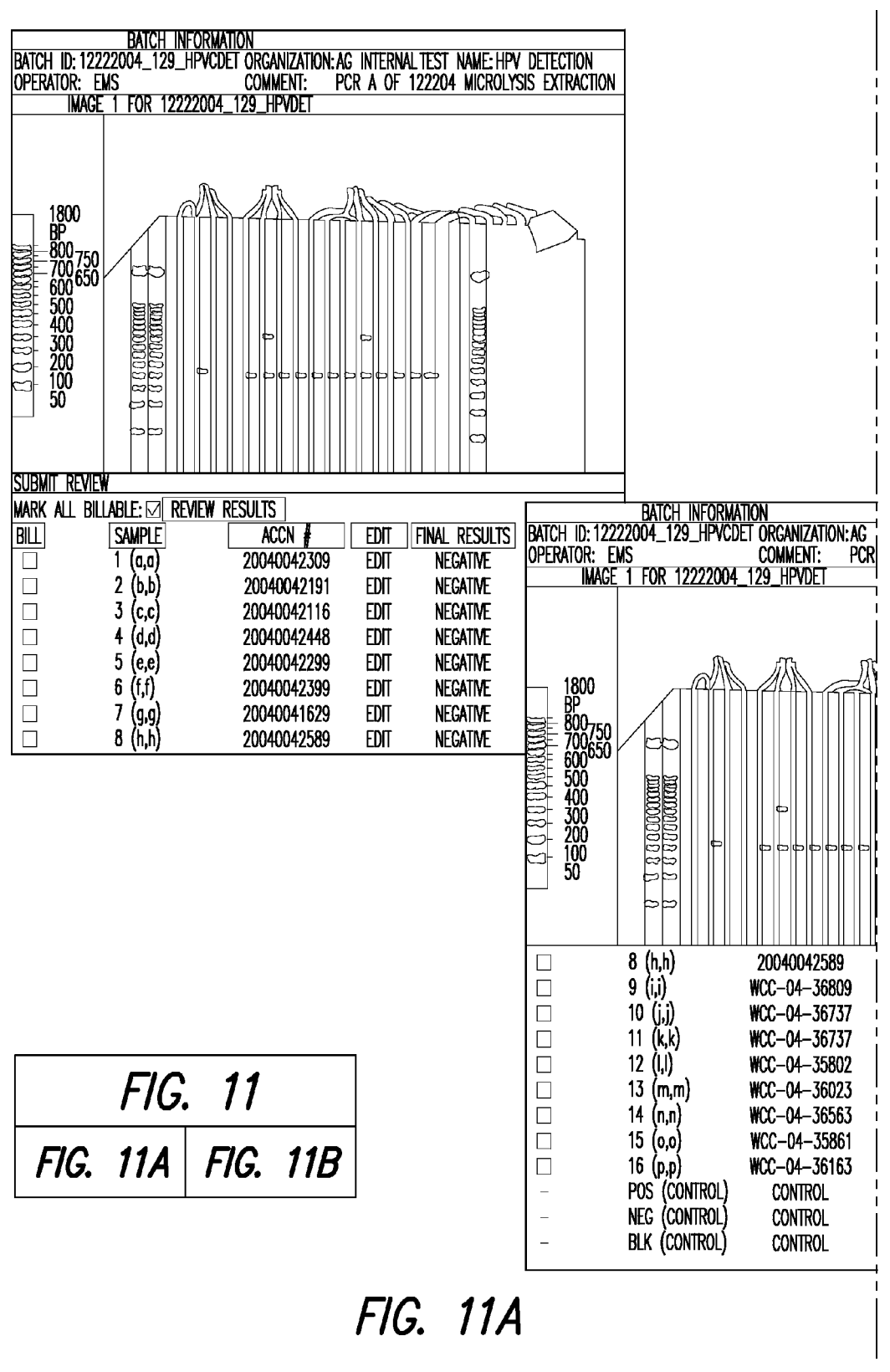
Figure 11B:
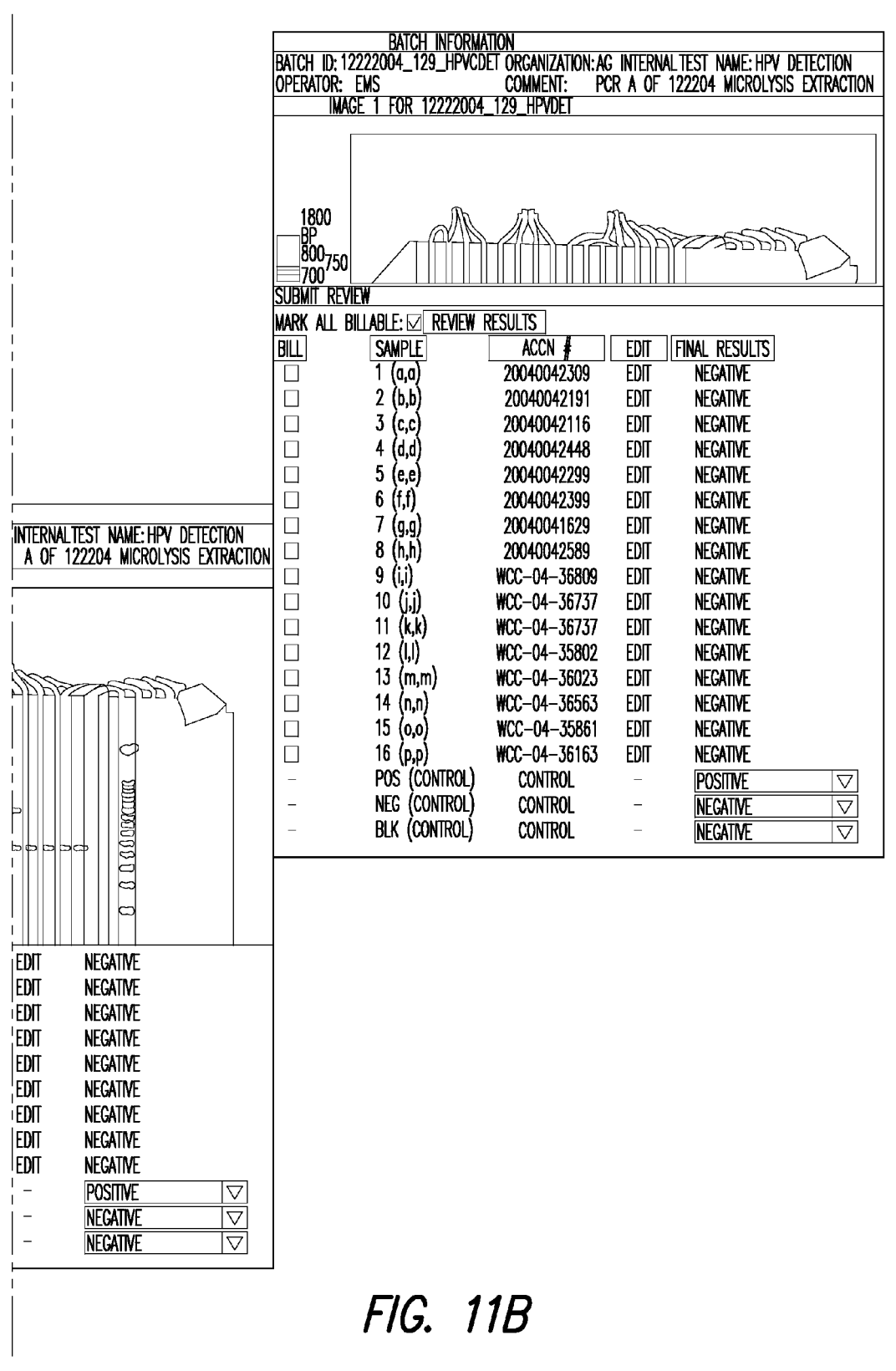

FIG. 11 illustrates split screen review of laboratory data in an interpretive data set;

FIG. 13 illustrates Bayesian risk calculation for cystic fibrosis and dependent variables including ethnicity, family and personal history of cystic fibrosis in the risk assessment model;

FIG. 14 illustrates a specific example of a risk assessment model 642 for inherited thrombophilia;

FIG. 15 illustrates the linked files where the modification and refinement of the patient information 130 can occur.

DETAILED DESCRIPTION OF THE INVENTION

Figure 1A:
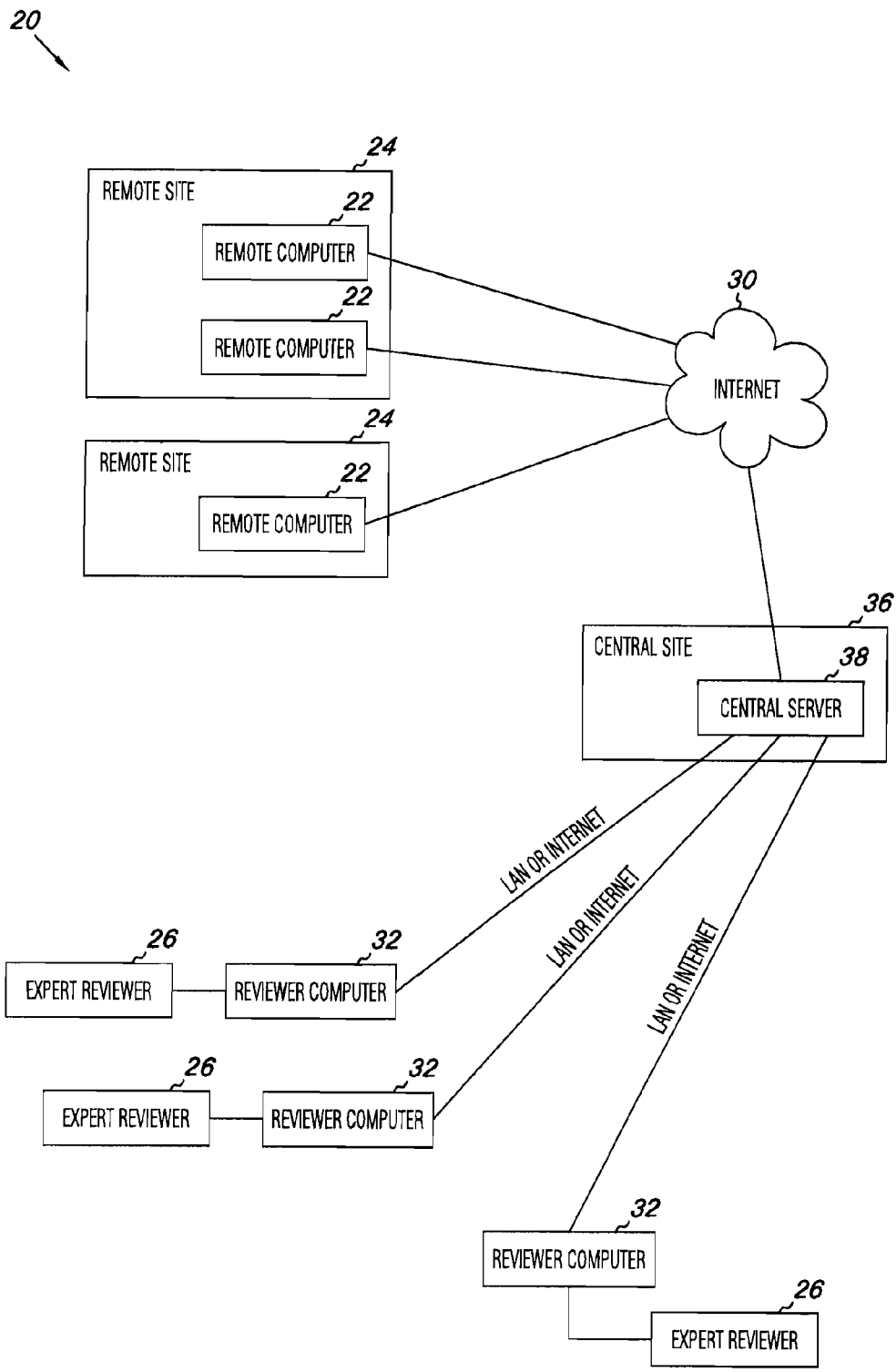
FIG. 1A illustrates an overview of the system with the remote computers, central server, and reviewer computers in a hub and spokes configuration.

The present invention may include systems, apparatus and methods as disclosed in the jointly owned U.S. application Ser. No. 10/409,337 filed Apr. 7, 2003 and entitled Genetic Test Apparatus and Method, the disclosure of which is hereby incorporated by reference in its entirety.

The present invention provides apparatus, systems and methods to perform individually and in an integrated manner laboratory operations 320 directed toward molecular diagnostic testing in a telemedicine model. In one embodiment, the system 20 controls the laboratory operations 320 of a molecular diagnostic test 50 at one or more remote sites 24 by computer from a central site 36 over the Internet 30. The system 20 collects information from the remote site 24 or sites and transmits that information to one or more expert reviewers 26 for analysis of the technical results and medical interpretation via Internet 30. The expert reviewer 26 may be located geographically near or distant from the remote site 24 or sites. The interpretation in the form of a test report 640 is transmitted back to the remote site 24.

Patient information 130 and specimens 220 from the patient are collected proximate to the remote site 24. The specimens 220 are then analyzed through a series of laboratory operations 320 that constitute the set of technical operations for a molecular diagnostic test 50 at the remote site 24. The laboratory operations 320 are directed toward molecular chemistries such as, for example, genetic chemistry and proteomic chemistry. The laboratory operations 320 produce a set of laboratory data 330. The system 20 collects the laboratory data 330 and the patient information 130 into an interpretive data set 430. The system 20 then transmits the interpretive data set 430 to an expert reviewer 26 for interpretation. The expert reviewer 26 is typically, but not necessarily, located at a site geographically distant from the remote site 24 where the laboratory operations 320 are conducted. The expert reviewer 26 interprets the interpretive data set 430, which is a combination of laboratory data 330 and patient information 130, and creates a test report 640. Expert systems 622, expert database 623, reference information 626, dynamic database tools 628, and interpretive comments 630 may be used by the expert reviewer t in interpreting the interpretive data set 430 and creating the test report 640. The interpretation of the interpretive data set 430 in the form of one or more test reports 640 is then transmitted back to the remote site 24 where the test report 640 may be utilized by a medical professional. The patient or other interested entities may also access the test report 640 at the remote site 24.

The system 20 may be monitored and controlled from a central site 36. The central site 36 may select the laboratory operations 320 to be performed at the remote site 24, and may choose the laboratory operations 320 based on the patient information 130. The central site 36 may also monitor the quality of the laboratory operations 320 conducted at the remote site 24, monitor the use of materials at the remote site 24, and may otherwise control the laboratory operations 320 at a remote site 24. Subsystems and methods that provide quality control, quality assurance and business trend analyses and generate corresponding reports are also included.

In general terms, the system 20 according to the present invention employs computers in communication with one another. The computers may, for example, be linked together through the Internet 30. Proprietary networks, LAN's, and other networks may also be used, at least in part.

Figure 1B:
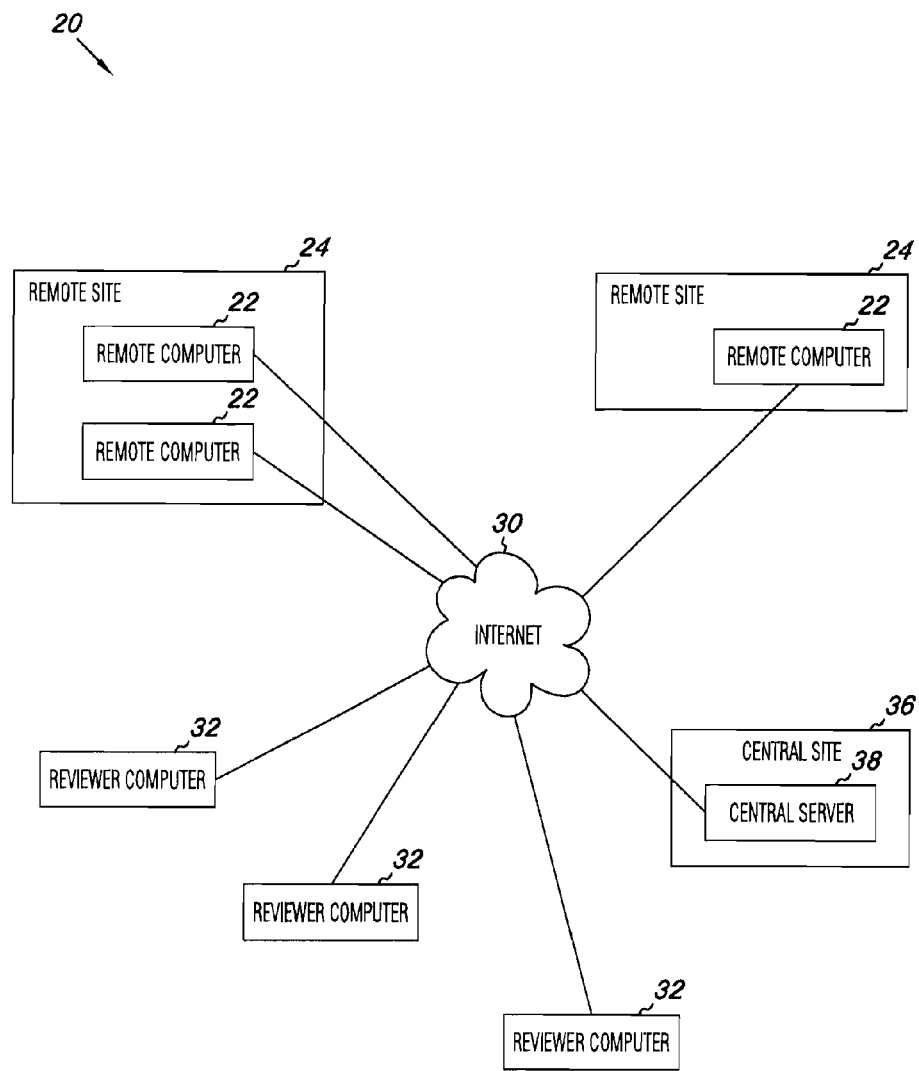
FIG. 1B illustrates an overview of the system with the remote computers, central server, and reviewer computers in a distributed configuration.

As shown in FIG. 1-A, the computers in the system 20 include one or more remote computers 22 with at least one remote computer 22 located at each of the one or more remote sites 24, a central server 38 configured as one or more computers and associated with the central site 36, and one or more reviewer computers 32 used by expert reviewers 26 to receive and review interpretive data sets 430. Each reviewer computer 32 is located proximate at least one expert reviewer 26. The central server 38 may host the system 20 software and control the system 20 by supporting communication over the Internet 30, monitoring the remote site 24, monitoring expert reviewers 26, and controlling the flow of data within the system 20.

The remote computer 22, the central server 38, and the reviewer computer 32 are linked by the Internet 30 or other computer network so that the remote computer 22, the central server 38, and the reviewer computer 32 may be at geographically dispersed locations. The remote computers 22, reviewer computers 32, and central server 38 shown in FIG. 1-A configured in a hub and spokes arrangement with the central server 38 acting as a hub and moderating the data flow in the system 20. The remote computer 22, central server 38, and reviewer computer 32 could be arranged in many other configurations. For example, FIG. 1-B shows a distributed network with the remote computers 22 interacting directly with other remote computers 22, the reviewer computers 32, and the central server 38 through the Internet 30.

The software that executes the system 20 according to the present invention may be divided into subsystems, the subsystems being hosted on the central server 38, the remote computer 22, and the reviewer computers 32. The subsystems may interact via the Internet 30 through a hub and spokes configuration as shown in FIG. 1-A or in a dispersed configuration as shown in FIG. 1-B. Communications between the remote computers 22, the reviewer computers 32, and the central server 38 may be encrypted or otherwise secure. Certain subsystems on the remote computers 22 or on the reviewer computers 32 may be configured as web browsers.

Figure 2:
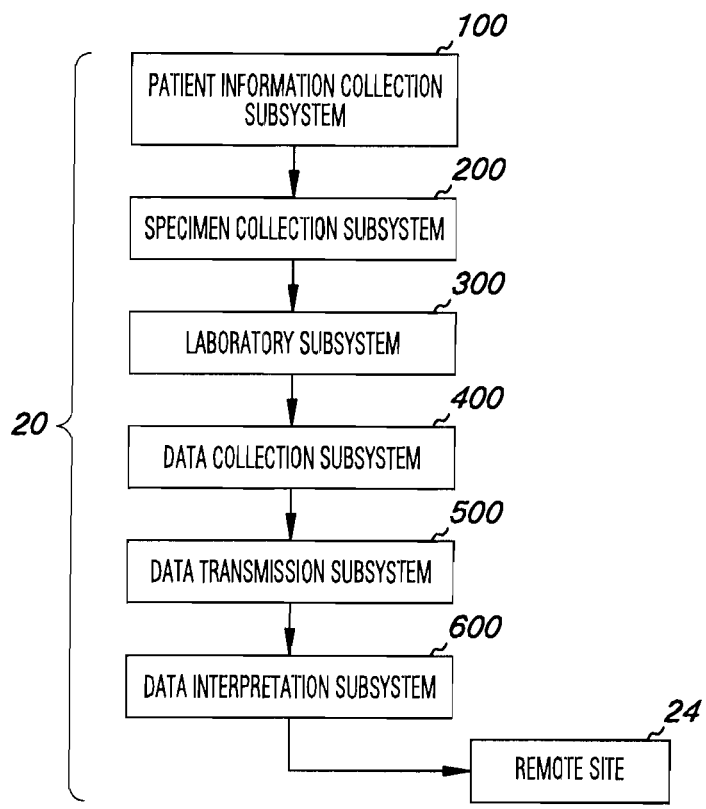
FIG. 2 illustrates the functional subsystems and the general flow of information between the functional subsystems.

In general functional terms, the system 20 comprises six major functional subsystems, as illustrated in FIG. 2. These six major functional subsystems are the patient information collection subsystem 100, specimen collection subsystem 200, laboratory subsystem 300, data collection subsystem 400, data transmission subsystem 500, and data interpretation subsystem 600. The system 20 may be configured as discrete sub-systems, each dedicated to a single functional component, or configured as a fully integrated system 20. Similarly, any or all of the individual functional components may be integrated into sub-systems. Thus, the following description should not necessarily be understood to define any physical or functional separation of the functional components, except as specifically described and required.

The general connection between these six major function subsystems and the flow of data between these six major functional subsystems is shown in FIG. 2. The patient information collection subsystem 100 collects patient information 130 and the specimen collection subsystem 200 collect specimens 220 from the patient proximate to the remote site 24. The specimens 220 are then analyzed through a series of laboratory operations 320 that constitute a molecular diagnostic test 50 at the remote site 24. The laboratory operations 320 are controlled by the laboratory subsystem 300. The laboratory operations 320 produce a set of laboratory data 330. The data collection subsystem 400 collects the laboratory data 330 and the patient information 130 into an interpretive data set 430. The data transmission subsystem 500 then transmits the interpretive data set 430 to an expert reviewer 26 for interpretation. The expert reviewer 26 is typically located at a site geographically distant from the remote site 24 where the laboratory operations 320 are conducted. The expert reviewer 26 aided by the data interpretation subsystem 600 interprets the interpretive data set 430, creates a test report 640. The data transmission subsystem 500 then transmits the test report 640 to the remote site 24 where the test report 640 can be utilized by a medical professional and the test report 640 can be accessed by the patient.

The patient information collection subsystem 100 collects information from the patient at the remote site 24 pertinent to the selection of molecular diagnostic tests 50 to be performed and the interpretation of the selected molecular diagnostic tests 50. Patient information 130 may include, for example, medical history, family history, lifestyle information, racial and ethnic background, reason for requesting a molecular diagnostic test 50, sample type, medical examination data, results from specialized studies, commentary from medical professionals, responses to questionnaires, responses to various stimuli, and performance responses to specified performance tasks. Billing information, insurance information, and other ancillary data may also be included in the patient information 130 or as a separate stand-alone file.

Figures 3, 3A, 3B:
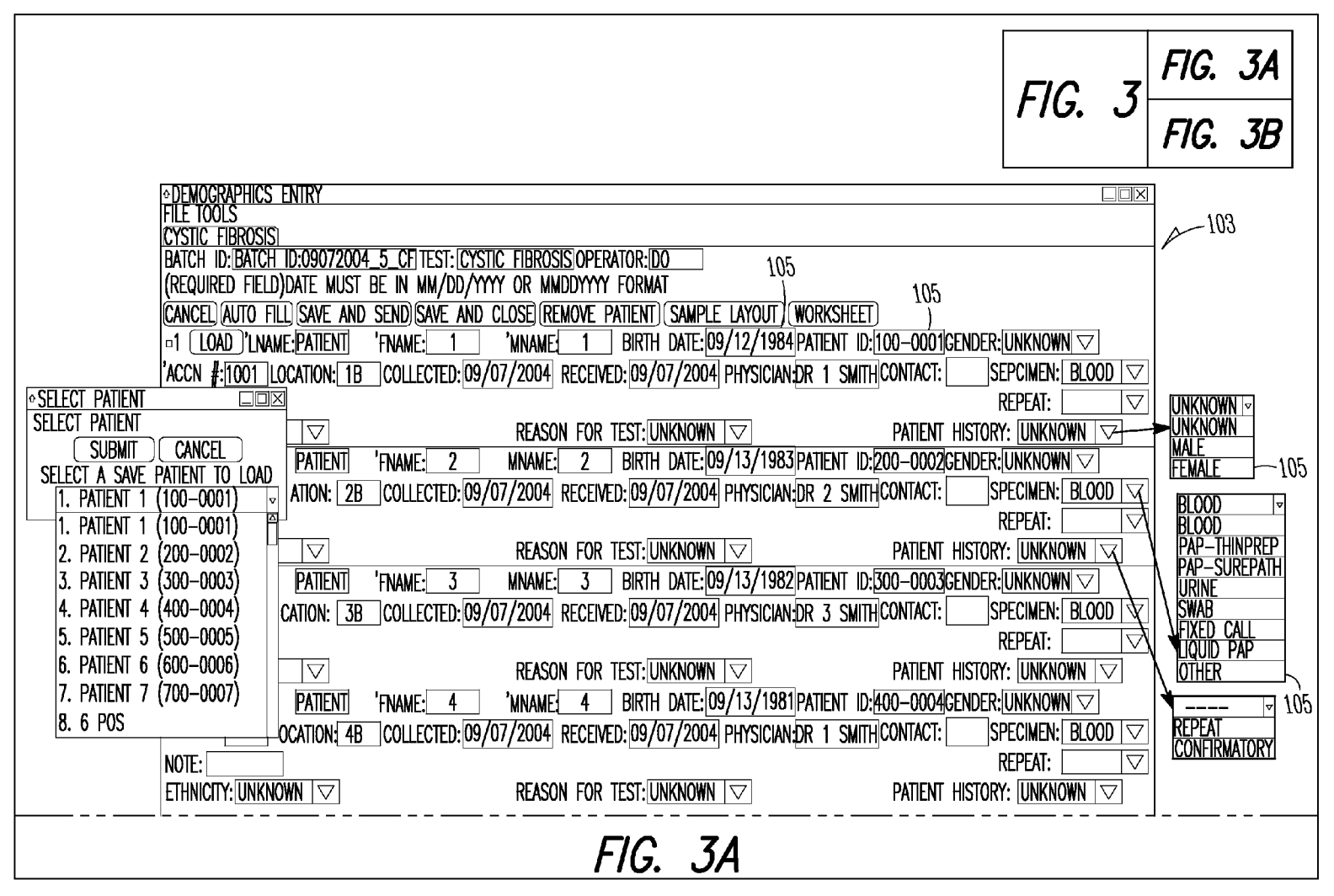
Figure 3B:
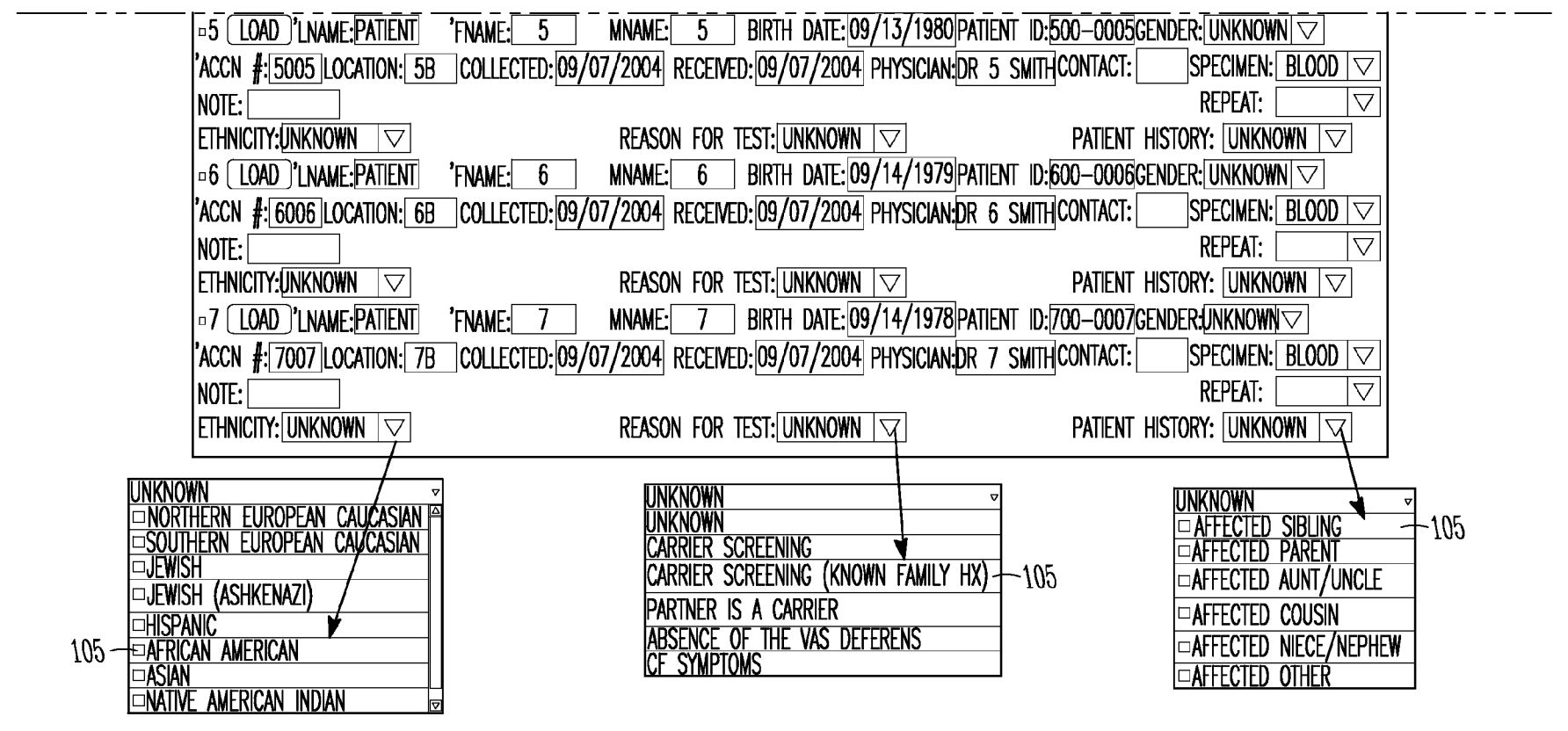

The patient information collection subsystem 100 may display an electronic form 103 on a remote computer 22 where the electronic form 103 has active data entry fields 105. Such data entry fields 105 would include fields for the entry of textual, visual, auditory, and performance information, and the data entry fields 105 could include, for example, various buttons, dials, pull down windows, highlighting features, box selection features, and text windows. FIG. 3 illustrates an electronic form 103 having data entry fields 105 for the entry of text data to identify a patient and their corresponding sample, medical and pathologic information, data entry by highlighting data elements on a pull down memo, and data entry by selection of boxes adjacent to data elements.

Patient information 130 may also be collected by optically scanning "bubbled in" responses to a questionnaire 110, by digitizing physiological data 125, by digitally recording the performance responses 115 to specified performance tasks such as the pattern of manipulation of some manipulative, and in other ways as would be readily understood by those skilled in the art.

Figure 4:
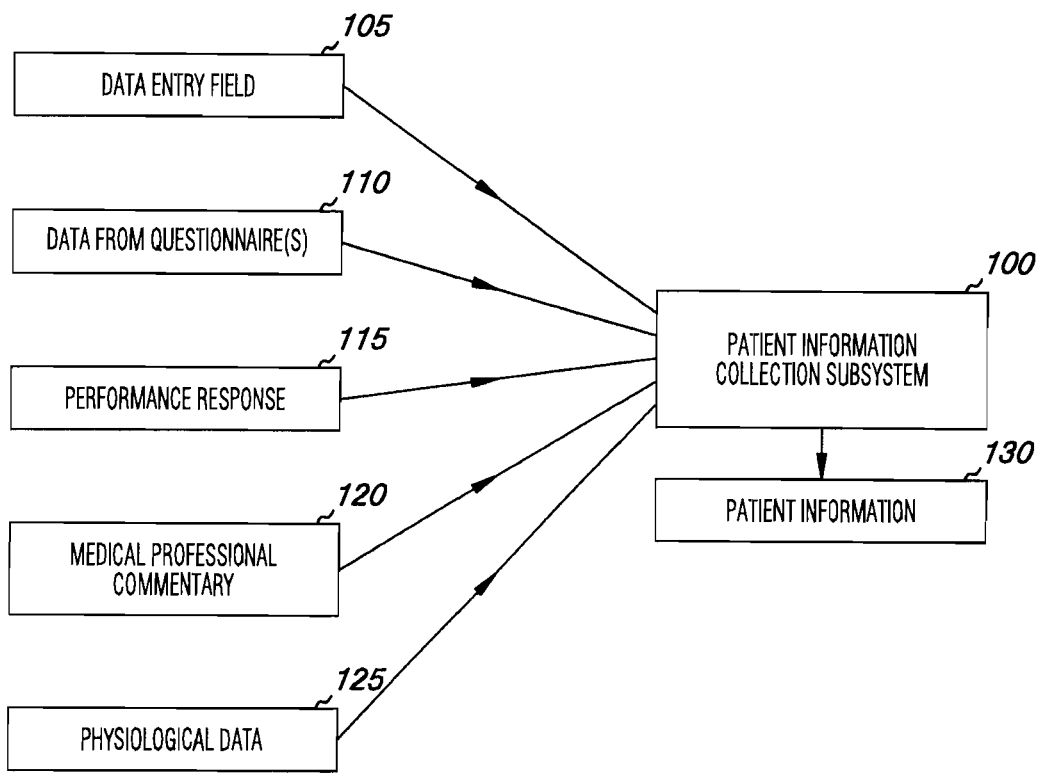
FIG. 4 illustrates the patient information subsystem showing flows of data from different data sources into the patient information dataset.

FIG. 4 illustrates patient information collection subsystem 100 collecting information from data entry fields 105, from digitized performance responses 115, from digitized responses to questionnaires 110, medical professional commentary 120 entered in text data entry fields 105, and physiological data 125 in digital form. The patient information collection subsystem 100 then integrates these various data so as to create a dataset of patient information 130 for a particular patient.

Figure 5:
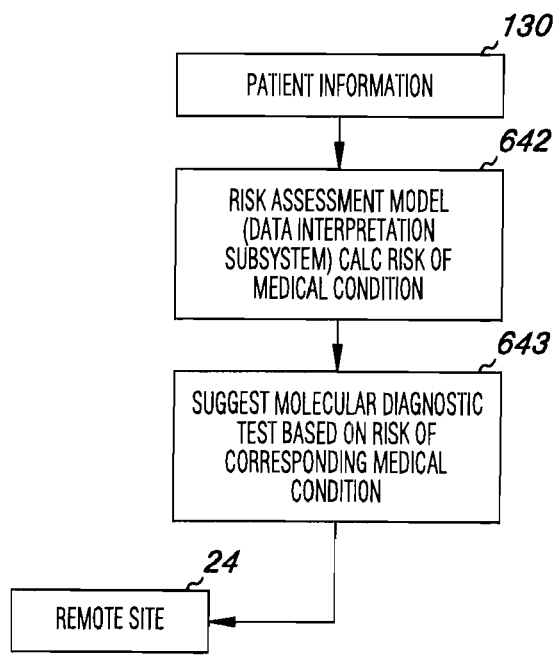
FIG. 5 illustrates the ability of the system to suggest molecular diagnostic tests based on risk.

If a specific molecular diagnostic test 50 has been requested, the patient information 130 may be tailored specifically to the molecular diagnostic test 50 being requested. Alternatively, the patient information 130 may be used for the selection of appropriate molecular diagnostic tests 50. This process is illustrated in FIG. 5, which shows the patient information 130 being input into a risk assessment model 642, which may be a subsystem of the data interpretation subsystem 600. The risk assessment model 642 analyzes the patient information 130 using statistical models to assess the patient's risk of certain medical conditions including disease predisposition and or resistance. The risk assessment model 642 may then suggest specific molecular diagnostic tests 50 based upon the particular patient's risk for the corresponding medical conditions. For example, a statistical model within the risk assessment model 642 may then use data abstracted from the patient information 130 related to a patient's family history and to signs or symptoms of cystic fibrosis. The risk assessment model 642 would then calculate the patient's risk for cystic fibrosis. The patient's risk for cystic fibrosis would then suggest the appropriateness of a molecular diagnostic test 50 directed toward diagnosis of cystic fibrosis.

The patient information 130 is used by various subsystems within the data interpretation subsystem 600 used in the interpretation of molecular diagnostic tests 50, as described below.

Figure 6A:
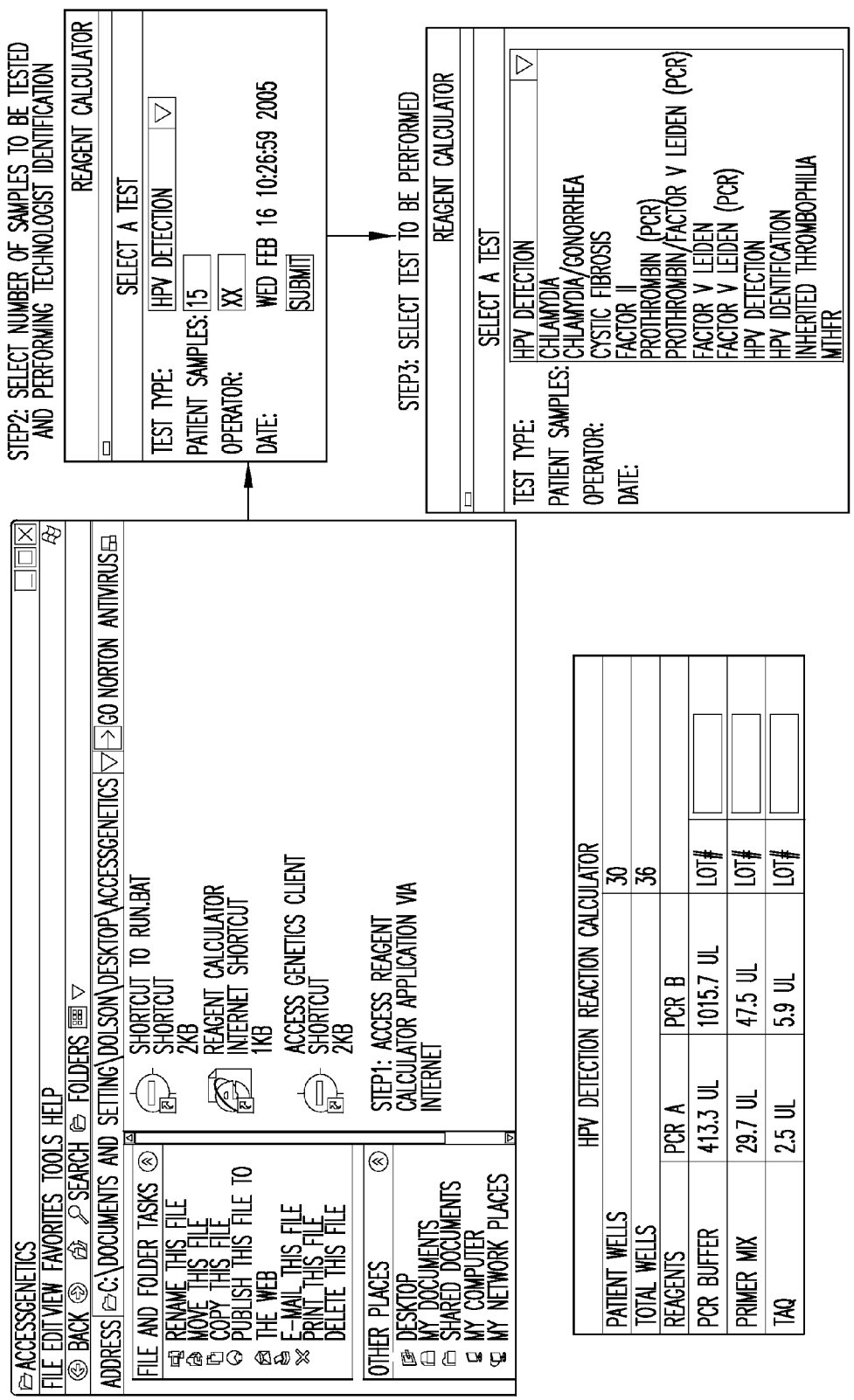
FIG. 6A illustrates the reagent calculator.
Figure 6B:
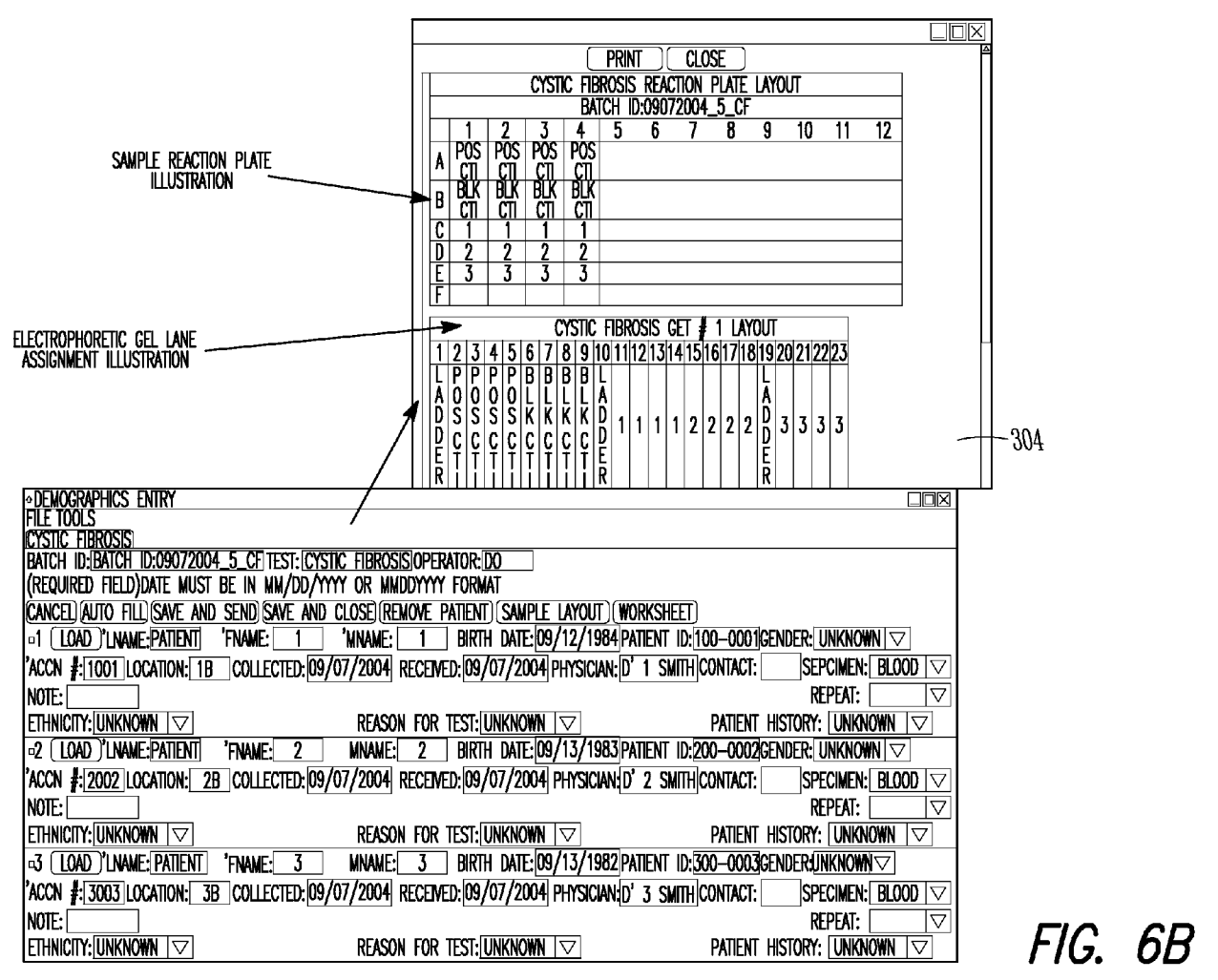

Specimens 220 are collected from the patient proximate to the remote site 24. The specimen collection subsystem 200 may include providing a kit 210, an example of which is illustrated in FIG. 6F, to the remote sites. The kit 210 may use existing technologies, along with all the necessary instructions and controls, to allow laboratory technicians having varying levels of training and skill to expertly obtain specimens 220 necessary for the relevant molecular diagnostic test 50 to be performed. Often the source of the specimen 220 dictates the amount of specimen 220 available for testing. The kit 210 is designed to accommodate these varying available sample volumes.

Specimens 220 to be tested by a molecular diagnostic test 50 may be obtained from the patient in an environment convenient for the patient, such as a hospital or physician's office, proximate to the remote site. The remote site 24 may be geographically distant from the central server 38 and from the expert reviewers 26 that interpret the laboratory data 330 and the patient information 130.

A variety of specimens 220 may be taken from the patient depending upon the nature of the molecular diagnostic test 50 being conducted. For example, DNA or RNA or various types of protein preparations from specimens 220 used for protein and genetic chemistries are most commonly extracted from peripheral blood. However, DNA or RNA specimens 220 may be extracted from a variety of other sources, such as, for example, exfoliated cells from a Pap smear sample, exfoliated cells from the oral cavity, or exfoliated cells from the buccal mucosa due to the unavailability of peripheral blood or because these alternative DNA or RNA specimens 220 lend themselves to more efficient genetic testing and in certain cases provide a more reliable and accurate test result. Multiple sources of cells suitable for testing DNA or RNA for thrombophilia genetic markers, Factor V Leiden and Prothrombin mutations, detection of mutation markers indicative of cystic fibrosis, human papillomavirus, gonorrhea, and chlamydia or herpes simplex detection by analyzing DNA or RNA nucleotides for mutation markers may also be used.

Similarly, the system 20 will provide information and the specific methods for the procurement of specimens 220 with the interest of preserving certain protein specifies. These may include fractionation of serum or plasma from blood and or prostatic and seminal fluid to derive the protein, prostatic specific antigen. This protein, properly procured can be submitted to the system 20 for analysis and subsequent transmission to the expert reviewer 26.

After the specimens 220 are obtained from the patient, the specimens 220 are analyzed at the remote site 24 through laboratory operations 320 that constitute a molecular diagnostic test 50. The laboratory subsystem 300 controls the laboratory operations 320 at the remote site 24 and assigns the specimens 220 to the appropriate laboratory operations 320.

The laboratory operations 320 are generally directed toward molecular chemistries such as, for example, genetic chemistry and proteomic chemistry that constitute a molecular diagnostic test 50. A batch of specimens 220 is a plurality of specimens 220 from one or more patients subject to the laboratory operations 320. Typically, laboratory operations 320 of a particular molecular diagnostic test 50 are conducted on a batch of specimens 222. The laboratory operations 320 produce a set of laboratory data 330 for each specimen 220. Collectively the data for the batch of specimens 222 is termed the batch data 324.

The specimens 220 are assigned to a batch of specimens 222. The laboratory operations 320 are then performed on the batch of specimens 222 to yield laboratory data 330 for each specimen 220.

The laboratory subsystem 300 may include providing a kit 210 to the remote site 24 that enables the remote site 24 to carry out the laboratory operations 320 of a molecular diagnostic test 50. The laboratory operations 320 may be directed toward molecular diagnostic tests 50 based in genetic chemistries or based in proteomic chemistries, and the laboratory operations 320 of the molecular diagnostic test 50 implement the genetic chemistry or the proteomic chemistry. The kit 210 includes reagents, laboratory equipment, laboratory supplies, supporting materials, and protocols.

The kit 210 organizes the collection of samples and organizes the laboratory operations 320 of a molecular diagnostic test 50. The kit 210 may include existing technologies, along with all the necessary instructions and controls, to allow laboratory technicians at the remote site 24 to expertly perform the laboratory operations 320 on the specimen. The kit 210 enables laboratory personnel having varying levels of training and skill to conduct consistent high quality laboratory operations 320.

For example, the kit 210 may organize the conduct of laboratory operations 320 directed toward a genetic chemistry, such as purification of specimens 220 by extracting the nucleic acid from the specimens 220, denaturing the purified nucleic acid and marking targeted fragments of the nucleic acid (i.e., performing the genetic chemistry) to identify characteristics of target genes, detecting the genetic data produced by the genetic chemistry, interpreting the targeted genetic data, and reporting the results.

The kit 210 may organize laboratory operations 320 directed toward genetic chemistry by implementing commercially available PCR (Polymerase Chain Reaction) approaches, including: (a) those known to involve quantitative methods involving PCR (b) those employing hybridization to fluorochrome labeled beads (c) those known to use miniaturization technologies such as hybridization chips, and those the leverage the mechanical, electrical and other physical characteristics of nucleic acid and protein species. Other laboratory operations 320 that may be implemented by the kit 210 include the meso and microscale bioassay technologies commercially available from a variety of sources, including the systems known by the trademarks Labchip by Caliper Technologies inc. and Infiniti from AutoGenomics, Inc.

In one embodiment, the kit 210 implements a non-PCR approach using a micro well incubation plate and a flourometer, which carries out the incubation. The flourometer may be connected to the Internet 30 so that the flourometer may be controlled by the system from the central site 36. Other suitable non-PCR approaches are commercially available from Third Wave Technologies, Inc. of Madison, Wis., USA under the trademark Invader and described in U.S. Pat. No. 6,214,545 entitled "Polymorphism Analysis By Nucleic Acid Structure Probing," U.S. Pat. No. 6,210,880 entitled "Polymorphism Analysis By Nucleic Acid Structure Probing With Structure-Bridging Oligonucleotides," and U.S. Pat. No. 6,194,149 entitled, "Target-Dependent Reactions Using Structure-Bridging Oligonucleotides."

The kit 210 may also be configured to organize the laboratory operations 320 directed toward proteomic chemistry. In addition, the kit 210 may include additional laboratory technologies for genetic chemistry and protein chemistry such as, agarose and polyacrylamide gel electrophoresis, capillary electrophoresis, fiber optic sensor devices, planar wave guide sensing devices, DNA or RNA nucleic acid micro arrays, micro mechanical biosensors, non-array based chip sensors, real-time fluorescence detectors, digital image capture, and fluorometers, all according to known analytic principles.

Figure 6E:
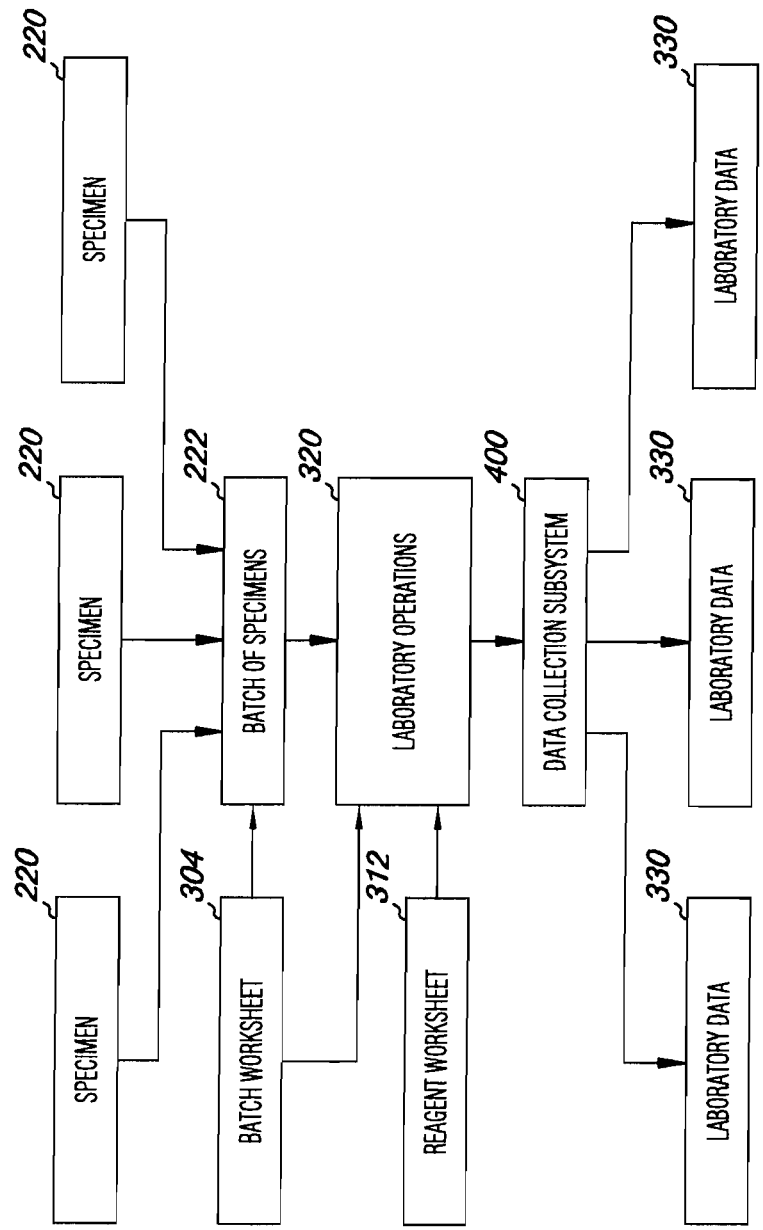
FIG. 6E illustrates operational flow and data flow in the laboratory subsystem.
Figure 6F:
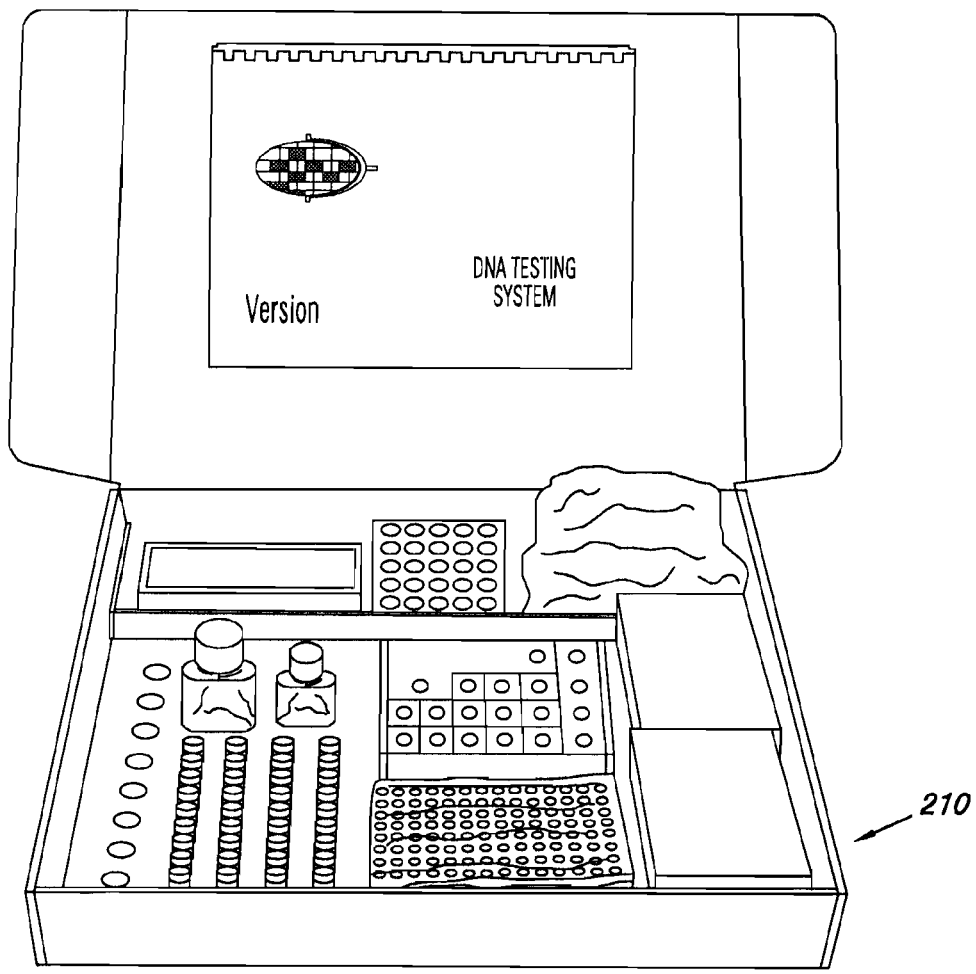
FIG. 6F illustrates an embodiment of a portion of the kit.

The laboratory subsystem 300 may display worksheets by computer for the laboratory operations 320 that may contain data entry fields 105 and may be web based, as shown in FIG. 6E. These worksheets aid technicians at the remote site 24 in the conduct of the laboratory operations 320. The worksheets include a reagent worksheet 312 that defines the volumes of reagents to be used in the laboratory operations 320 and a batch worksheet 304 that summarizes the laboratory operations 320 and assigns the specimens 220 to particular locations within the various apparatus during the laboratory operations 320.

For example, a reagent worksheet 312 defines the precise volumes of each of the reagents used in the laboratory operations 320, as shown in FIG. 6A, based on the number of specimens 220 included in a particular batch. This calculation anticipates the inclusion of reagent volumes for a set of positive and negative controls and also allows for wastage and overage. The worksheet may include data entry fields 105 for the entry of the reagent lot number and expiration date for each reagent. The reagent lot numbers and expiration dates may be used in quality control monitoring as well as inventory tracking. The laboratory subsystem 300 may include flagging a warning to the laboratory technologist of the expiration of a particular reagent or that a particular fault has been noted with a particular lot of reagent that may adversely affect a laboratory operation.

A batch worksheet 304 summarizes the workflow of the laboratory operations 320, and may assign a particular specimen in a batch of specimens 222 to a particular physical position on, for example, the racks, plates and gels during the laboratory operations 320 of a molecular chemistry, as shown in FIGS. 6B, 6C, and 6D. For example, the assignment of a specimen can generate a label and a position in a reaction plate and in an electrophoretic gel.

In a similar manner, the laboratory subsystem 300 may assign each specimen 220 in a given batch of specimens 222 a particular position for each sample tube in the plastic rack used in the final step of the DNA extraction operation, the position on the plastic rack used in the process of thermocycling, and finally the position of that resulting DNA sample on each of a series of electrophoretic apparatus (gels and or capillary or arrays). The laboratory subsystem 300 anticipates the possibility of a sample(s) failing, and the re-assignment of that failed sample on a new batch list and the corresponding assignment to each subsequent operation involving that assay.

Results of each laboratory operation may be reported so that the flow of laboratory operations 320 may be monitored from the central site 36. Laboratory instruments may be monitored so the progress of a laboratory operation and the status of a particular specimen involved in the laboratory operation may be monitored from the central site 36.

The data collection subsystem 400 creates sets of digital data from the laboratory data 330 and also correlates the laboratory data 330 with patient information 130. The digitized laboratory data 330, patient information 130, and other data from the remote site 24 collected by the data collection subsystem 400 may then be transmitted to other computers including the central server 38 and reviewer computers 32 by the data transmission subsystem 500.

Figure 7:
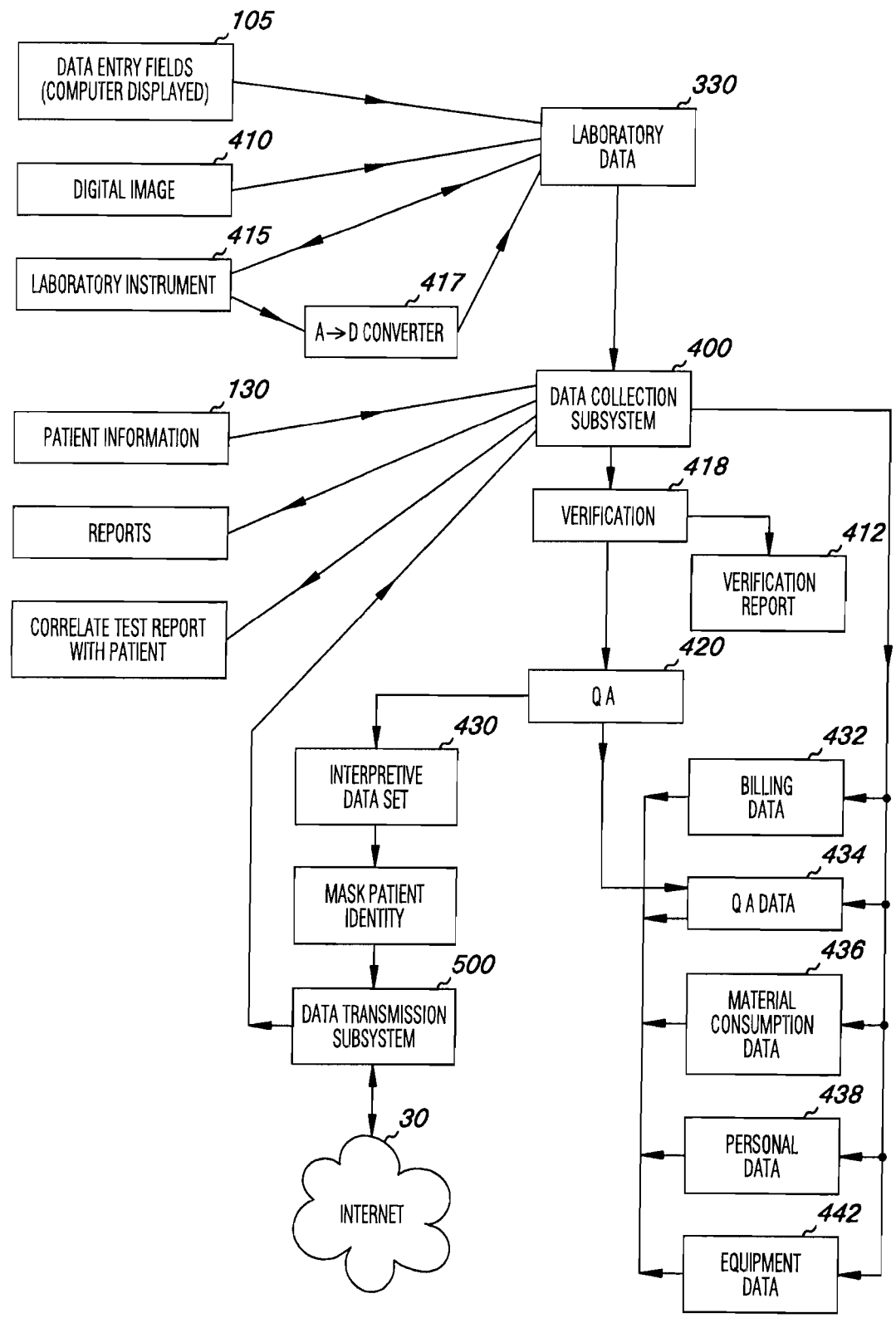
FIG. 7 illustrates the operations and data flows in the data collection subsystem.

The laboratory data 330, which is raw analytic data, may consist of observations, measurements, data from laboratory instruments 415, and the like, which must then be converted into digital format. An embodiment of the data collection subsystem 400, illustrated in FIG. 7, uses computer networking techniques and systems to electronically gather data with as little human involvement as possible.

The conversion of laboratory data 330 into digital format may be accomplished by manual entry of the laboratory data 330 into computer displayed data entry field 105 by personnel at the remote site 24 or may be automatically loaded directly from the local laboratory information system. The data entry fields 105 could include, for example, various buttons, dials, and text windows. Digital images 410 could be included in the laboratory data 330, such as, for example, an image of an electrophoretic gel containing processed DNA specimens 220. The digitization of the laboratory data 330 may include creation of a software interface to an analog data source such as a laboratory instrument through an A to D converter 417.

The laboratory instrument 415 may be configured to produce digital data and to interact with other computers in the system over the Internet 30. For example, the data collection subsystem 400 may allow the central server 38 to address a laboratory instrument 415 configured as a fluorometer over the Internet 30 to query the flourometer in order to determine the status of the flourometer. The data collection subsystem 400 periodically ceases incubation and then reads the reaction plate to determine if that operation is complete or incomplete. The data collection subsystem 400 interprets the control in each reaction plate to determine if an adequate level of fluorescence signal has been created. If the reaction is complete, then the data collection subsystem 400 prompts the interpreter to read the plate, otherwise the plate is returned to the incubation mode, and the process is repeated later in time. The data collection subsystem 400 is designed to control aspects of laboratory operations 320 such as heating sources, mechanical movement of the plate and or plate holder, mechanical agitation of reactions and the operation of the readout functions of the machine.

The data collection subsystem 400, which may be hosted at the remote site 24, may also include a verification subsystem 418, which conducts a preliminary review of laboratory data 330 and patient information 130 to determine the existence of data necessary for interpretation of the molecular diagnostic test 50. If insufficient or inconsistent laboratory data 330 or patient information 130 has been collected, the verification subsystem 418 generates a verification report 412 for the remote site 24 that identifies the insufficient data or inconsistent data and generates recommendations to correct the problem. The data collection subsystem 400 may include a quality assurance subsystem 420 capability based on mathematical representations and/or transformations of the laboratory data 330. Such capabilities could also be provided in the data interpretation subsystem 600.

After gathering, verifying, and assuring the quality of the laboratory data 330 and the patient information 130, the data collection subsystem 400 generates an interpretive data set 430. The interpretive data set 430 contains patient information 130 for a particular patient and laboratory data 330 resulting from laboratory operations 320 conducted on specimens 220 obtained from the patient. The data collection subsystem 400 then transmits the interpretive data set 430 through the data transmission subsystem 500 to the expert reviewer 26 for review.

The data collection subsystem 400 protects patient identity. The data collection subsystem 400 may mask all patient identification data in the interpretive data set 430, meaning data that could be used to identify the patient, from laboratory data 330 related and patient information 130. Under this alternative, the interpretive data set 430 does not include any patient identification data. When test reports 640, as described below, are transmitted back to the remote site 24, the data collection subsystem 400 at the remote site 24 may then correlate the patient identification with the test report 640. In this manner, no data positively linked to a named patient ever leaves the remote site 24. This arrangement greatly increases the private nature of the entire remote molecular diagnostic testing procedure.

Alternatively, the data collection subsystem 400 may separate the laboratory data 330 and the patient information 130 into two separate files, a confidential information file that contains confidential information and a non-confidential information file that contains non-confidential information. The confidential information file does not include any patient identification data. The confidential information file and the non-confidential information file may be transmitted separately, including the transmission through different transmission modalities and at different times. The central site 36 or other receiving site may then correlate the information file and the non-confidential information file to perform the required interpretations and analysis necessary to generate the test report 640.

Another alternative is for the data collection subsystem 400 to encrypt, using any convenient encryption technology, any portion of the information to be transmitted.

Any or all of these data preparation alternatives may be used in any desired combination to ensure the safe, secure and confidential transmission of the interpretive data set 430 and any other patient information 130.

The data collection subsystem 400 assigns an identifier to the patient information 130 such that the patient information 130 may be linked to a particular specimen 220 and the specimen 220 may be linked to a particular patient.

Additional data sets may also be generated by the data collection subsystem 400 at the remote site. These data sets, for example, may include billing data 432, quality assurance data 434, material consumption data 436, personnel data 438, and equipment data 442. These additional data sets would typically be transmitted to the central server 38 for use at the central site 36.

Figure 8:
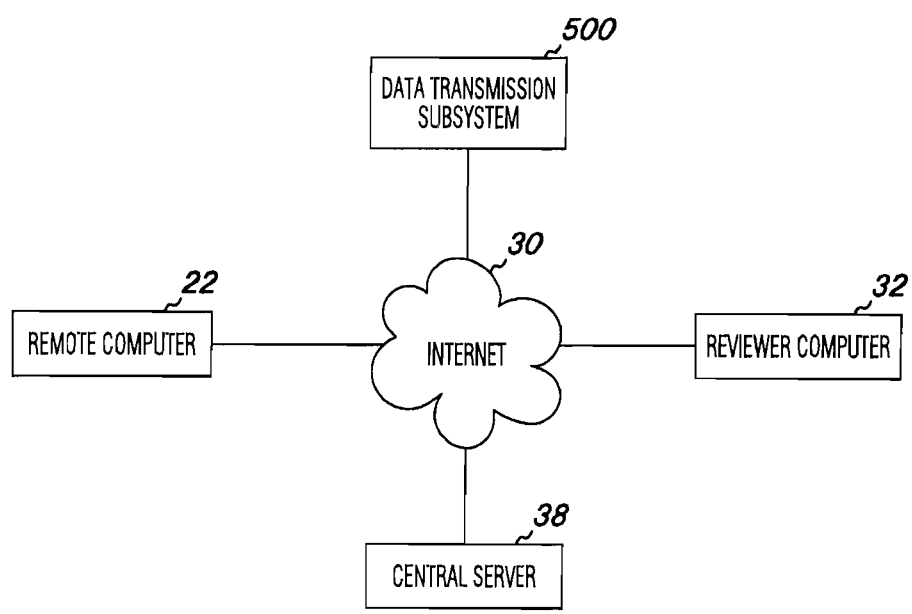
FIG. 8 illustrates the data transmission subsystem refereeing the exchange of data between a remote computer, the central server, and the reviewer computer over the Internet.

The data transmission subsystem 500, illustrated in FIG. 8, referees the transmission of data from the remote computer 22 to other computers in the system 20, particularly the central server 38 and the reviewer computer 32. The central server 38 may be in a geographic location different from the remote site 24 that performs the laboratory operations 320. Data transmission may be accomplished using any convenient data transmission scheme. In one embodiment, the remote computer 22 transmits the data to the central server 38 over the Internet 30. Other networks and other modes of data transmission may also be used, for example, writing the data to electronic, optical, or magnetic media and transporting the media by mail to the central site 36.

As illustrated in FIG. 9, the data transmission subsystem transmits data from the remote site including the interpretive data set 430 and remote site data 446 to the data interpretation subsystem 600. Remote site data 446 includes billing data 432, quality assurance data 434, material consumption data 436, personnel data 438, and equipment data 442.

The expert reviewer 26, an individual with the appropriate skills, licenses, and other qualifications, interprets the interpretive data set 430. The expert reviewer 26 accesses the interpretive data set 430 by the reviewer computer 32. The interpretive data set 430 contains all of the data that may be required by the expert reviewer 26 for the expert reviewer 26 to interpret the molecular diagnostic test 50. The data interpretation subsystem 600 moderates the interaction of the expert reviewer 26 with the interpretive data set 430. The reviewer computer 32 may be geographically distant from the remote site 24, may be geographically distant from the central server 38, and may be geographically distant from the central site 36.

Figure 9A:
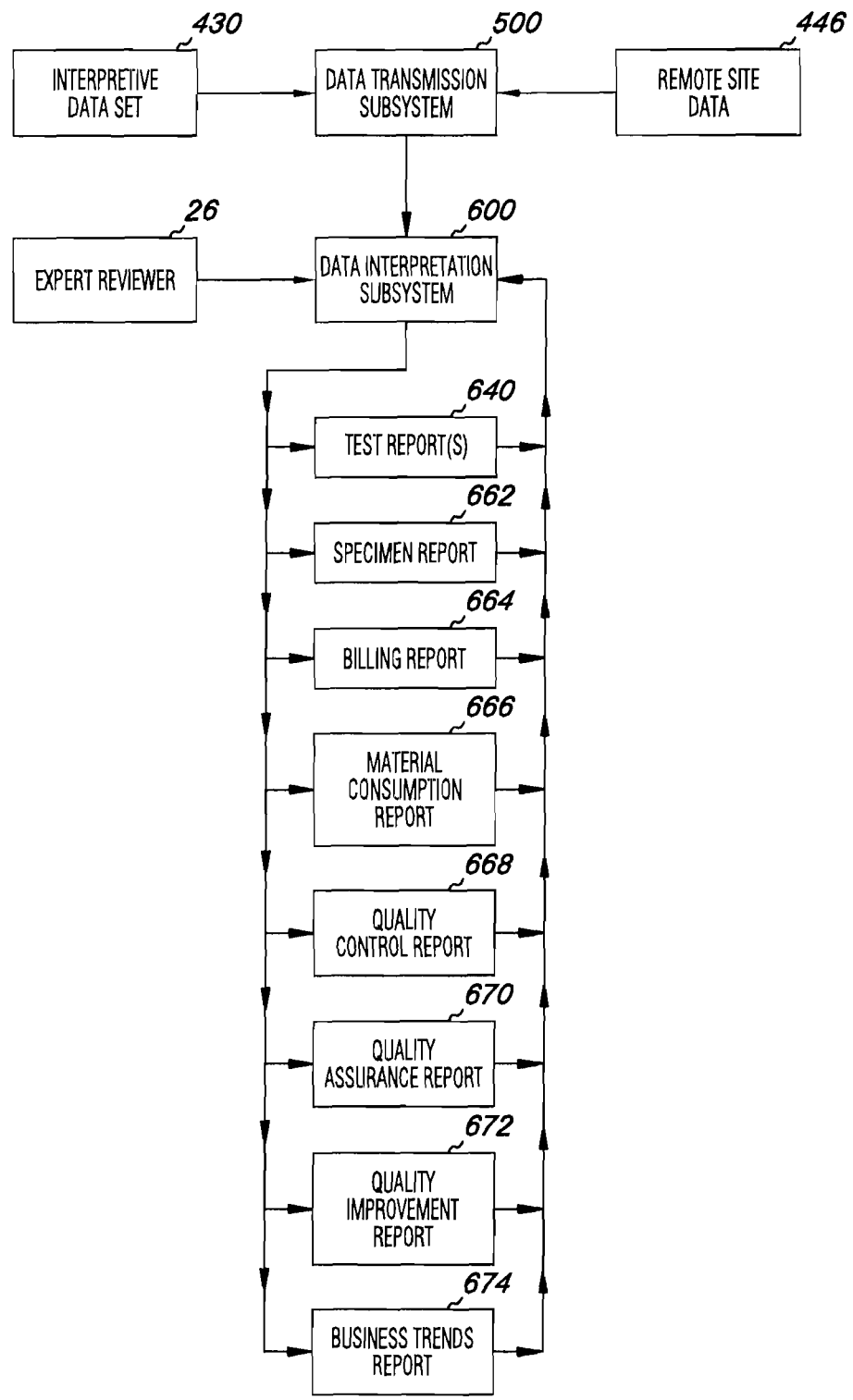
FIG. 9A illustrates the flow of operations and information in the data interpretation subsystem.

An embodiment of the data interpretation subsystem 600 is illustrated in FIG. 9A. The data interpretation subsystem 600 may notify an expert reviewer 26 that an interpretive data set 430 is available for interpretation by, for example, sending a text message or e-mail to the expert reviewer 26.

Figure 10:
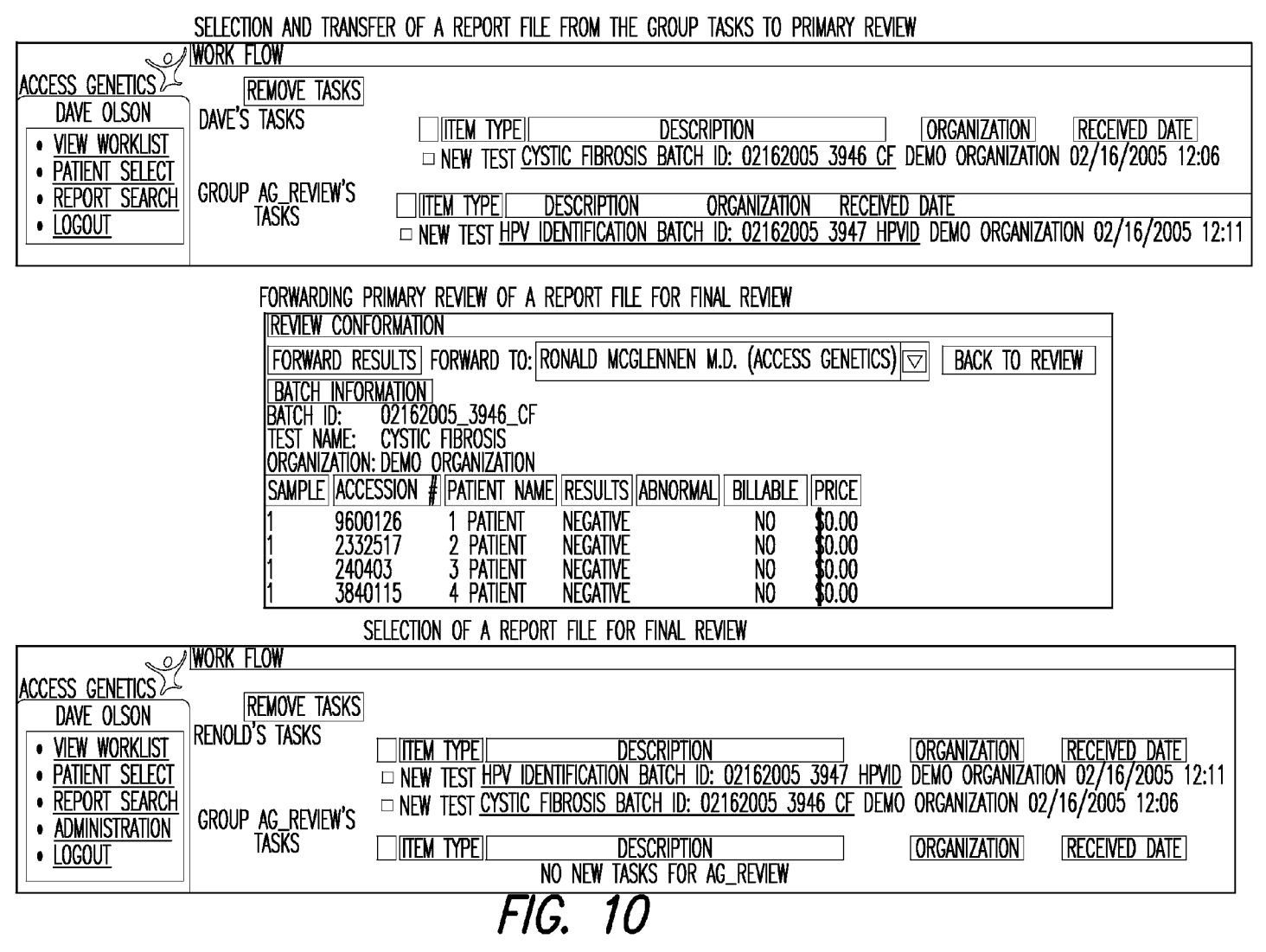

The data interpretation subsystem 600 may designate more than one expert reviewer 26 to review an interpretive data set 430 and link the reviews, as shown in FIG. 10. For example, the data interpretation subsystem 600 may designate a primary expert reviewer 26 and a confirmation expert reviewer 26. The prompting messages may be sent in series, i.e., the primary reviewer receives the first message to review the interpretive data set 430. When the primary expert review is complete, the data interpretation subsystem 600 notifies the confirmation expert reviewer 26 that an interpretive data set 430 is available for interpretation. When the confirmation review is completed, the data interpretation subsystem 600 sends a test report 640 to the remote site 24. The test report 640 may contain the expert reviewer's 26 interpretation of the molecular diagnostic test 50.

Figure 9B:
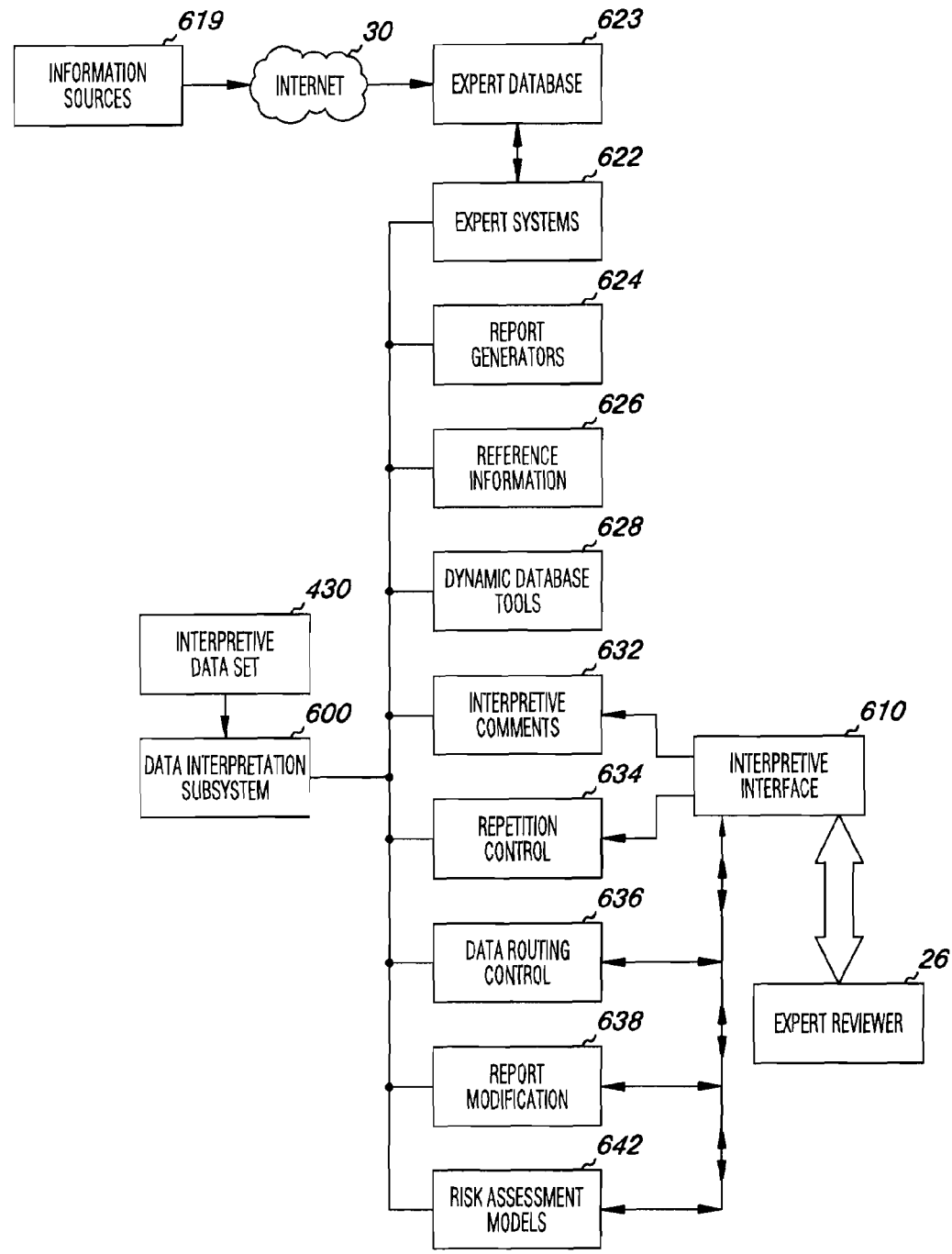
FIG. 9B illustrates the expert reviewer interacting with elements of the data interpretation subsystem.

The data interpretation subsystem 600 may provide an interpretive interface 610, as shown in FIG. 9B, on the reviewer computer 32 through which the expert reviewer 26 may login and then render interpretations of the interpretive data set 430, which are collected in a test report 640. The interpretive interface 610 includes a report generator 624 that allows the expert reviewer to produce a test report 640 that includes risk assessment statements, expert reviewer comments, and technical recommendations.

The technical recommendations may be embodied in a pull down menu feature of the interpretive interface 610, that, in one embodiment, offers choices to re-extract the DNA from the sample, repeat the gene chemistry step with twice the amount of added DNA, dilution of the current stock DNA, or to render the interpretation that there is insufficient sample for the reporting of a result, i.e. QNS or quantity not sufficient.

When the primary expert reviewer 26 completes the review of the interpretive data set 430, the test report 640 may be forwarded to the confirming expert reviewer 26. The data interpretation subsystem 600 may notify the confirming expert reviewer 26 of the availability of the test report 640 from the primary expert reviewer 26 by electronic messaging. When the test report 640 is at the Confirm File status, the interpretive data set 430 may again be interpreted, additional comments rendered, or other variation of the above. The completion of the confirmation mode may be achieved when the Confirm Results button is deployed. Control of the test report 640 is then shifted to the data transmission subsystem 500, which then transmits the test report 640 to the remote site 24.

A number of specialized tools can be embedded into the data interpretation subsystem 600, as illustrated in FIG. 9B.

Figure 12B:
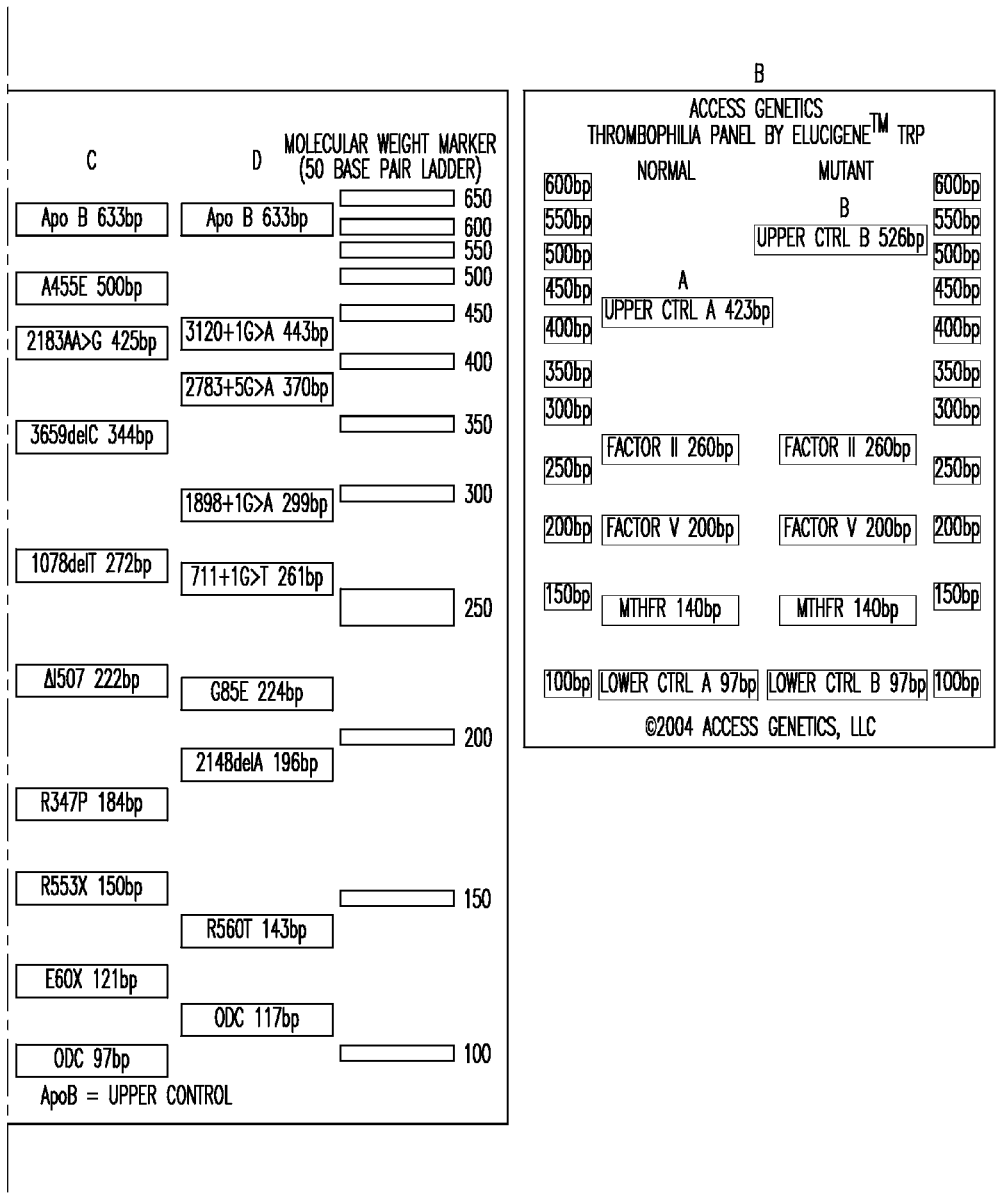
FIG. 12 illustrates cystic fibrosis (A) and inherited thrombophilia (B) interpretation guides in a dynamic database tool.

These tools may be, for example, embodied in the form of linked web pages containing reference information 626, interpretative comments 632, and dynamic database tools 628 to analyze aspects of the test results. For example, a dynamic database tool 628 called the PapFinder™ is a relational database that contains the pattern of DNA fragment resulting from the digestion of PCR derived DNA used in the detection of the virus human papillomavirus. PapFinder™ is a tool through which the interpreter can decipher the complexity of DNA bands on an electrophoretic gel that are characteristic of the various HPV genotypes. Another example is a dynamic database tool 628 for the interpretation of the bands of DNA in a selected set of mutations in molecular diagnostic tests 50 for cystic fibrosis and molecular diagnostic tests 50 for inherited thrombophilia, as illustrated in FIG. 12. The data interpretation subsystem 600 may include similar dynamic database tools 628 useful in the interpretation of DNA fragment run by gel electrophoresis or similar technologies, for example, dynamic database tools 628 directed toward genetic analysis of osteoporosis, inherited colon cancer, inherited cardiovascular disease and clonal rearrangements of genes involved in leukemia and lymphoma.

Additional features of the data interpretation subsystem 600 include the repetition control 634, which can allow the expert reviewer 26 to command the repetition of laboratory operations 320, and data routing control 636, which controls the routing of the resulting laboratory data 330 through the data interpretation subsystem 600.

Similarly, the data interpretation subsystem 600 may allow may include report modification 638, which allows the expert reviewer 26 to modify a previously issued test report 640 through the Search Results link and the action to modify a specific test report 640 via the Modify Review link button. The interpretation of the molecular diagnostic test 50 and the corresponding patient information 130 may be modified or updated via the Custom Comment and Customize Patient information links.

The data interpretation subsystem 600 may include risk assessment models 642 that analyze the interpretive data set 430 to create and present a patient specific risk assessment of disease based upon the combination of patient information 130 and laboratory data 330 in the interpretive data set 430. For example, patient information 130 such as the patient's stated ethnicity, the presence or absence of a personal or family history of cystic fibrosis, and the laboratory data 330 from molecular diagnostic test 50 for a defined number of mutations in the cystic fibrosis gene, may be used to calculate the Bayesian risk of that patient carrying a mutation in that gene. The resulting Bayesian risk statement is automatically provided in the test report 640. FIG. 13 illustrates several examples results of the risk assessment model 642 for cystic fibrosis. The data interpretation subsystem 600 also anticipates patients having a complex ethnicity or family history and includes algorithms in the risk assessment models 642 for the calculation of Bayesian probability in such complex cases.

The data interpretation subsystem 600 may include risk assessment for the probability of a disease to progress toward a more severe condition based on archived and updateable data set of similar test information, such as in the example of the oncogenic risk of infection by the various types of human papillomavirus detected in sample of cervicovaginal cells and registered against the current and past morphologic samples from the same individual.

Another embodiment of the data interpretation subsystem 600 may include risk assessment models 642 that provide the calculation of a risk assessment for a series of related or unrelated gene mutations that cooperate to impart an additive or synergistic risk of disease, calculated by means other than a Bayesian probability. For example, the risk of a patient for the development of deep venous thrombosis, a complication of inherited thrombophilia, may be demonstrated from a series of 1-3 independent gene markers, as well as the effect of other demographic, pharmacologic and environmental factors relevant to that patient. FIG. 14 illustrates a specific example of a risk assessment model 642 for inherited thrombophilia. Additional risk assessment models 642 may also be included for polygenic and disease states with multiple causes such as osteoporosis, cardiovascular disease, and various cancers.

The interpretive interface 610 may be configured to customize the interpretative comments 632 from changes made to the patient information 130. In the normal course of clinical laboratory testing, there is often the need to include more patient information 130, which in turn will influence the interpretive comments 632 to be used in the creation of the risk assessment statement and any recommendations for therapy in the test report 640. The present invention may provide a link whereby selected patient information 130 may be included in the test report 640 and correspondingly prompt the construction of the more accurate and relevant interpretive comments 632 comments for inclusion in the test report 640. FIG. 15 illustrates the linked files where the modification and refinement of the patient information 130 can occur.

The interpretive interface 610 may include an expert system 622 that incorporates information derived from the medical and scientific literature. The expert system 622 includes an expert database 623 constructed from information sources 619 one or more of a variety of commercially available software products that incorporates information from information sources. These information sources 619 may be public or proprietary sources such as Medline, PubMed, Compendex, GeneBank, www.genetest.com and www.webmd.com. The expert system 622 contains large amounts of prewritten information pertaining to various clinical and pathologic aspects of the medical conditions associated with the molecular diagnostic tests 50. The expert database 623 is derived from the manual and automated review of the medical and scientific literature obtained from the public and from the proprietary sources. The expert system 622 collates information into the expert database 623 from the information sources 619 based on prescribed keywords that are specific to a medical condition, a molecular diagnostic test 50, and a clinical condition.

The expert system 622 then sorts the expert database 623 based on the expert reviewer's 26 interpretation of the molecular diagnostic test 50 in combination with the patient information 130 contained in the interpretive data set 430 to locate pertinent references and comments that are, in turn, presented to the expert reviewer 26. This combination of sorting criteria reduces the set of selected comments and references presented to the expert reviewer 26 to those pertinent to the specific patient and interpretation of the molecular diagnostic test 50. The comments may include, but are not limited to, diseases associated with a particular molecular diagnostic test 50 interpretation, risk, and options for therapy. The expert system 622 then presents these comments and references to the expert reviewer 26, who may then incorporate the comments, the references, and information in the references into the test report 640.

After the expert reviewer 26 or reviewers have interpreted the interpretive data, set 430, the data interpretation subsystem 600 generates one or more test reports 640. In one embodiment, the data interpretation subsystem 600 generates both a technical test report 640 directed to the medical professional, and a separate non-technical test report 640 directed to the patient. The Internet 30, other networks, and other recognized data transmission modes then securely transmit the test report 640 to the remote site 24. The test report may also be produced in an electronic format suitable for being interfaced into the remote site's laboratory information system.

The data interpretation subsystem 600 or other subsystems within the system may generate additional reports that may be transmitted to the central site 36, to a remote site 24, and to an expert reviewer 26 as appropriate by the data transmission subsystem 500. These additional reports may include a specimen report 662 listing each specimen 220 in a batch of specimens 222 analyzed in a specific laboratory operations 320, a billing report 664 listing the information needed to provide billing codes and listing the price of services rendered, a material consumption report 666 directed toward monitoring of material consumption, quality control report 668, quality assurance report 670, quality improvement report 672, and business trends report 674.

The data interpretation subsystem 600 may identify technical problems in the performance of the test steps done at the remote site 24 that require added samples or steps to ensure a quality test result. Such problems may then be identified to the remote site 24 so that corrective actions may be taken at the remote site.

Repetition control 634 may include the option to report the specimen 220 as pending, occurring whenever the operation command is to repeat or revise the specimen 220 or batch data 324. The repetition control 634 may further provide a series of pull down menus listing options for possible repeat laboratory operations 320 for a wide variety of molecular diagnostic tests 50, such as a provision to repeat an extraction other or additional techniques, the recommendation to add more cycles of amplification through a specific gene chemistry procedure and the choice of added analytic methods. The use of the repeat commands generates a message through the system 20 to place that specimen 220 into the next batch queue or into a new or designated batch of specimens 222. Correspondingly, the message to repeat a specific specimen 220 will be flagged in the new batch worksheet 304.

The foregoing discussion discloses and describes merely exemplary embodiments of the present invention. It should be understood that no limitation of the scope of the invention is intended thereby. Upon review of the specification, one skilled in the art will readily recognize from such discussion, and from the accompanying drawings and claims, that various changes, modifications and variations can be made therein without departing from the spirit and scope of the inventions as defined in the following claims.

What is claim is:

1. A method for remotely interpreting laboratory data, comprising:
   a. obtaining a specimen from a patient at a remote site;
   b. obtaining patient and specimen information;
   c. performing clinical laboratory operations on the patient specimen at the remote site;
   d. collecting clinical laboratory data, and patient and specimen information at the remote site using a computer;
   e. transmitting one or more sets of clinical laboratory data, patient and specimen information to a central site, by Internet;
   f. generating, at the central site, one or more interpretive patient data sets from the combined transmitted clinical laboratory data, patient and specimen information, using a computer;

g. transmitting one or more interpretive patient data sets from the central site to one or more expert reviewers by Internet;
h. interpreting one or more interpretive patient data sets by one or more expert reviewers;
i. generating, using a computer, one or more test reports under the control of one or more expert reviewers; and,
j. transmitting one or more test reports to the remote site by Internet.

2. The method of claim 1, further providing an interpretive interface to the one or more expert reviewers.

3. The method of claim 2, wherein the interpretive interface is configured to have an expert system.

4. The method of claim 2, wherein the interpretive interface is configured to have a report generator.

5. The method of claim 2, wherein the interpretive interface is configured to have dynamic database tools.

6. The method of claim 2, wherein the interpretive interface is configured to provide interpretive comments.

7. The method of claim 2, wherein the interpretive interface is configured to provide repetition control.

8. The method of claim 2, wherein the interpretive interface is configured to provide data routing control.

9. The method of claim 2, wherein the interpretive interface is configured to provide report modification.

10. The method of claim 2, wherein the interpretive interface is configured to have a risk assessment model.

11. The method of claim 2, wherein the expert system comprises an expert database.

12. The method of claim 1, further comprising providing a data interpretation subsystem.

13. The method of claim 12, wherein the data interpretation subsystem generates at least a report selected from the group consisting of a test report, a specimen report, a billing report, a material consumption report, a quality control report, a quality assurance report, a quality improvement report, and a business trends report.

14. The method of claim 12, wherein the data interpretation subsystem comprises a risk assessment model, wherein the risk assessment model uses patient information to suggest a molecular diagnostic test.

15. A method for practicing telemedicine, comprising:
a. providing a computer network comprising at least a central server and a remote computer in communication with one another, the central server located at a central site and the remote computer located at a remote site;
b. obtaining a specimen from a patient at a remote site;
c. obtaining patient and specimen information;
d. analyzing the patient specimen to produce clinical laboratory data at the remote site;
e. inputting the patient and specimen information and the clinical laboratory data into the remote computer at the remote site;
f. transmitting the patient and specimen information and the clinical laboratory data over the computer network to the central computer at the central site by Internet;
g. providing one or more expert reviewers at the central site;
h. interpreting the patient and specimen information and the clinical laboratory data by one or more expert reviewers at the central site;
i. generating a report comprising the interpretation of the patient and specimen information and the clinical laboratory data by one or more expert reviewers, using a computer; and,
j. transmitting the report from the central site to the remote computer at the remote site by Internet.

16. The method of claim 15, further comprising the use of a data interpretation subsystem by one or more expert reviewers to interpret the patient and specimen information and clinical laboratory data.

17. The method of claim 15, wherein a data interpretation subsystem is used to moderate the interaction between one or more expert reviewers, and the patient and specimen information and clinical laboratory data.

18. The method of claim 1, wherein the laboratory operations comprise one or more molecular diagnostic tests.

19. The method of claim 1, wherein the patient information is transmitted to the central site before the laboratory operations are performed.

20. The method of claim 19, wherein the central site determines the laboratory operations to be performed on the specimen and transmits the laboratory operations to be performed to the remote site by the Internet.

21. The method of claim 5, wherein the dynamic database tools are tools for inventory tracking, quality control, quality analysis, repetition control, data routing control, relational databases, report modification, interpretation of molecular diagnostic tests, interpretation of electrophoresis, and genetic analysis, or a combination thereof.

* * * * *